United States Patent
Durkin et al.

(10) Patent No.: US 9,365,494 B2
(45) Date of Patent: *Jun. 14, 2016

(54) PROCESS FOR SYNTHESIS OF AMINO-METHYL TETRALIN DERIVATIVES

(75) Inventors: Kieran Durkin, Folsom, CA (US); Lawrence Emerson Fisher, Mountain View, CA (US); Arthur Meili, Weisslingen/ZH (CH); Michaelangelo Scalone, Fideris GR (CH); Xianqing Shi, Clifton, NJ (US); Justin Vitale, San Mateo, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 606 days.

This patent is subject to a terminal disclaimer.

(21) Appl. No.: 13/359,329

(22) Filed: Jan. 26, 2012

(65) Prior Publication Data

US 2012/0323040 A1  Dec. 20, 2012

Related U.S. Application Data

(63) Continuation of application No. 12/637,548, filed on Dec. 14, 2009, now Pat. No. 8,119,842.

(60) Provisional application No. 61/138,596, filed on Dec. 18, 2008.

(51) Int. Cl.
| | | |
|---|---|---|
| C07C 231/18 | (2006.01) | |
| B01J 31/24 | (2006.01) | |
| C07C 315/02 | (2006.01) | |
| C07C 319/14 | (2006.01) | |
| C07C 319/20 | (2006.01) | |
| B01J 31/18 | (2006.01) | |

(52) U.S. Cl.
CPC ........... *C07C 231/18* (2013.01); *B01J 31/1805* (2013.01); *B01J 31/24* (2013.01); *B01J 31/2409* (2013.01); *C07C 315/02* (2013.01); *C07C 319/14* (2013.01); *C07C 319/20* (2013.01); *B01J 2231/645* (2013.01); *B01J 2531/821* (2013.01); *C07B 2200/07* (2013.01); *C07C 2102/10* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,376,712 | B2* | 4/2002 | Narizuka et al. | 564/385 |
| 7,312,359 | B2* | 12/2007 | Greenhouse et al. | 564/147 |
| 8,119,842 | B2* | 2/2012 | Durkin et al. | 564/162 |

* cited by examiner

*Primary Examiner* — Clinton Brooks

(57) ABSTRACT

Methods for producing a compound of formula k1 or k2

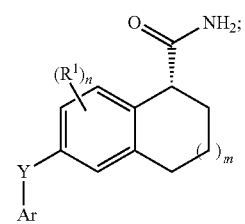

k1

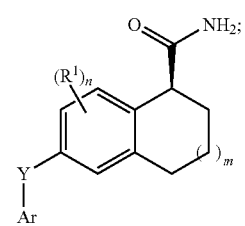

k2 by reducing a dihydronapthalene amide compound of formula i

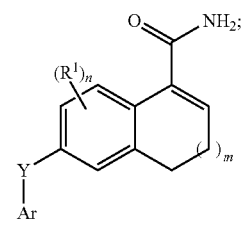

i with hydrogen gas in the presence of a ruthenium catalyst of formula j1 or j2

$Ru(Z)_2(L)$   j1;

$Ru(E)(E')(L)(D)$   j2;

wherein m, n, Ar, Y, $R^1$ E, E', D, Z and L are as defined herein.

17 Claims, No Drawings

US 9,365,494 B2

PROCESS FOR SYNTHESIS OF AMINO-METHYL TETRALIN DERIVATIVES

CROSS REFERENCE TO RELATED APPLICATIONS

This Application is a Continuation of U.S. application Ser. No. 12/637,548 filed on Dec. 14, 2009 now U.S. Pat. No. 8,119,842, which is entitled to the benefit of U.S. Provisional Application No. 61/138,596, filed Dec. 18, 2008, the disclosures of which are incorporated herein by reference.

FIELD OF THE INVENTION

This invention relates to processes for making substituted indane and tetralin compounds that are useful for enhancing cognitive memory in patients and for treating various central nervous system diseases.

BACKGROUND OF THE INVENTION

The actions of 5-hydroxytryptamine (5-HT) as a major modulatory neurotransmitter in the brain are mediated through a number of receptor families termed 5-HT1, 5-HT2, 5-HT3, 5-HT4, 5-HT5, 5-HT6, and 5-HT7. Based on a high level of 5-HT6 receptor mRNA in the brain, it has been stated that the 5-HT6 receptor may play a role in the pathology and treatment of central nerve system disorders. In particular, 5-HT2-selective and 5-HT6 selective ligands have been identified as potentially useful in the treatment of certain CNS disorders such as Parkinson's disease, Huntington's disease, anxiety, depression, manic depression, psychoses, epilepsy, obsessive compulsive disorders, mood disorders, migraine, Alzheimer's disease (enhancement of cognitive memory), sleep disorders, feeding disorders such as anorexia, bulimia and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. Such compounds are also expected to be of use in the treatment of certain gastrointestinal (GI) disorders such as functional bowel disorder. See for example, B. L. Roth et al., J. Pharmacol. Exp. Ther., 1994, 268, pages 1403-14120, D. R. Sibley et al., Mol. Pharmacol., 1993, 43, 320-327, A. J. Sleight et al., Neurotransmission, 1995, 11, 1-5, and A. J. Sleight et al., Serotonin ID Research Alert, 1997, 2(3), 115-8.

While some 5-HT6 and 5-HT2A modulators are known, there continues to be a need for compounds that are useful for modulating the 5-HT6 receptor, the 5-HT2A receptor, or both.

SUMMARY OF THE INVENTION

The invention provides a method of producing a compound of formula k1 or k2

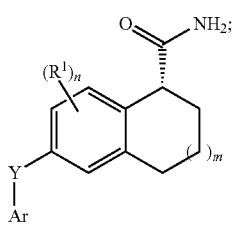

k1

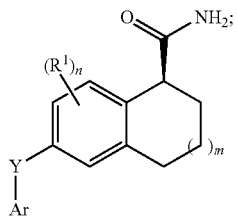

k2 wherein:
m is 0 or 1;
n is from 0 to 3;
Ar is: aryl; or heteroaryl, each of which may be optionally substituted with: halo; $C_{1-6}$alkyl; $C_{1-6}$alkoxy; cyano; hydroxy; $C_{1-6}$alkylsulfonyl; or halo-$C_{1-6}$alkyl;
Y is —O—; —S(O)$_p$— or —N—R$^a$ wherein p is from 0 to 2 and R$^a$ is hydrogen or $C_{1-6}$alkyl; and
R$^1$ is: halo; $C_{1-6}$alkyl; $C_{1-6}$alkoxy; or halo-$C_{1-6}$alkyl;
the method comprising:
reducing a dihydronapthalene amide compound of formula i

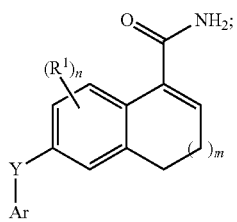

i with hydrogen gas in the presence of a Ruthenium catalyst of formula j1 or j2

$$Ru(Z)_2(L) \qquad j1;$$

$$Ru(E)(E')(L)(D) \qquad j2$$

wherein:
D is an optionally chiral diamine;
E and E' are both halo, or E is hydrogen and E' is BH$_4$;
L is a chiral diphosphine ligand; and
Z is: halo or R$^b$—CO$_2^-$ (carboxylate) wherein R$^b$ is: $C_{1-6}$alkyl; halo-$C_{1-6}$alkyl; $C_{1-6}$alkoxy; aryl optionally substituted with halo; or heteroaryl optionally substituted with halo.

The method is useful for preparation of compounds that are effective modulators of the 5-HT$_6$ receptor. Also disclosed are compounds useful as intermediates in the methods of the invention.

DETAILED DESCRIPTION OF THE INVENTION

Definitions

Unless otherwise stated, the following terms used in this application, including the specification and claims, have the definitions given below. It must be noted that, as used in the specification and the appended claims, the singular forms "a", "an," and "the" include plural referents unless the context clearly dictates otherwise.

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" means a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkylcarbonyl" means a moiety of the formula —C(O)—R', where R' is alkyl as defined herein. The term "Acyl may be used interchangeably with "Alkylcarbonyl".

"Alkylsulfonyl" means a moiety of the formula —R'—R", where R' is —SO$_2$— and R" is alkyl as defined herein.

"Alkylsulfonylalkyl means a moiety of the formula —R'—R"'—R"' where where R' is alkylene, R" is —SO$_2$— and R"' is alkyl as defined herein.

"Alkylamino means a moiety of the formula —NR—R' wherein R is hyrdogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein. "Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, optionally substituted phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof. Preferred aryl are phenyl and napthyl, and more prefereably phenyl, which may be optionally substituted as defined below.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylalkyl" means a group of the formula —R—R' wherein R is alkylene and R' is aryl as defined herein.

"Arylsulfonyl" means a group of the formula —SO$_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Cycloalkyl" means a monovalent saturated carbocyclic moiety consisting of mono- or bicyclic rings. Cycloalkyl can optionally be substituted with one or more substituents, wherein each substituent is independently hydroxy, alkyl, alkoxy, halo, haloalkyl, amino, monoalkylamino, or dialkylamino, unless otherwise specifically indicated. Examples of cycloalkyl moieties include, but are not limited to, cyclopropyl, cyclobutyl, cyclopentyl, cyclohexyl, cycloheptyl, and the like, including partially unsaturated derivatives thereof.

"Cycloalkylalkyl" means a moiety of the formula —R'—R", where R' is alkylene and R" is cycloalkyl as defined herein.

"Heteroalkyl" means an alkyl radical as defined herein wherein one, two or three hydrogen atoms have been replaced with a substituent independently selected from the group consisting of —$OR^a$, —$NR^bR^c$, and —$S(O)_nR^d$ (where n is an integer from 0 to 2), with the understanding that the point of attachment of the heteroalkyl radical is through a carbon atom, wherein $R^a$ is hydrogen, acyl, alkyl, cycloalkyl, or cycloalkylalkyl; $R^b$ and $R^c$ are independently of each other hydrogen, acyl, alkyl, cycloalkyl, or cycloalkylalkyl; and when n is 0, $R^d$ is hydrogen, alkyl, cycloalkyl, or cycloalkylalkyl, and when n is 1 or 2, $R^d$ is alkyl, cycloalkyl, cycloalkylalkyl, amino, acylamino, monoalkylamino, or dialkylamino. Representative examples include, but are not limited to, 2-hydroxyethyl, 3-hydroxypropyl, 2-hydroxy-1-hydroxymethylethyl, 2,3-dihydroxypropyl, 1-hydroxymethylethyl, 3-hydroxybutyl, 2,3-dihydroxybutyl, 2-hydroxy-1-methylpropyl, 2-aminoethyl, 3-aminopropyl, 2-methylsulfonylethyl, aminosulfonylmethyl, aminosulfonylethyl, amino sulfonylpropyl, methylaminosulfonylmethyl, methylaminosulfonylethyl, methylaminosulfonylpropyl, and the like.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

"Heteroarylalkyl" or "heteroaralkyl" means a group of the formula —R—R' wherein R is alkylene and R' is heteroaryl as defined herein.

"Heteroaryloxy" means a group of the formula —O—R wherein R is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —$CF_3$), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, homopiperazinyl, azepinyl, pyrrolidinyl, pyrazolidinyl, imidazolinyl, imidazolidinyl, pyridinyl, pyridazinyl, pyrimidinyl, oxazolidinyl, isoxazolidinyl, morpholinyl, thiazolidinyl, isothiazolidinyl, quinuclidinyl, quinolinyl, isoquinolinyl, benzimidazolyl, thiadiazolylidinyl, benzothiazolidinyl, benzoazolylidinyl, dihydrofuryl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, preferably one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl and 2-(hydroxymethyl)-3-hydroxypropyl "Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Polar aprotic solvent" means a solvent comprised of molecules having polar groups thereon, but without mobile protons. Exemplary polar aprotic solvents include, without limitation, dimethyl formamide, acetonitrile, dimethyl sulfoxide, N,N-dimethyl acetamide, N-methylpyrrolidinone, tetrahydrofuran, dioxane, ethyl acetate, tetrahydropyran, pyridine, acetone, 2-propanone, 2-butanone, ethylene glycol dimethyl ether, methylene chloride, chloroform, and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$—NR'R" wherein R', R" and R'" each independently is hydrogen or alkyl.

"Optionally substituted", when used in association with "aryl", "phenyl", "heteroaryl" "cycloalkyl", "heterocyclyl", or "aniline" means an aryl, phenyl, heteroaryl, cyclohexyl, heterocyclyl or aniline which is optionally substituted independently with one to four substituents, preferably one or two substituents selected from alkyl, cycloalkyl, cycloalkylalkyl, heteroalkyl, hydroxyalkyl, halo, nitro, cyano, hydroxy, alkoxy, amino, acylamino, mono-alkylamino, di-alkylamino, haloalkyl, haloalkoxy, heteroalkyl, —COR (where R is hydrogen, alkyl, phenyl or phenylalkyl), —(CR'R")$_n$—COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$—CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). Certain preferred optional substituents for "aryl", "phenyl", "heteroaryl" "cycloalkyl" or "heterocyclyl" include alkyl, halo, haloalkyl, alkoxy, cyano, amino and alkylsulfonyl. More preferred substituents are methyl, fluoro, chloro, trifluoromethyl, methoxy, amino and methanesulfonyl.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like. Preferred examples of a leaving group are halo, H$_2$N— or CH$_3$COO—. Particularly preferred are chloride, H$_2$N— or CH$_3$COO—.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tert-butanol, dioxane, pyridine, and the like. Unless specified to the contrary, the solvents used in the reactions of the present invention are inert solvents.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of this invention rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoro-acetyl, acetamido, benzyl (Bn), benzyloxycarbonyl (car-bobenzyloxy, CBZ), p-methoxybenzyloxycarbonyl, p-ni-trobenzyloxycarbonyl, tert-butoxycarbonyl (BOC), and the like. The artisan in the art will know how to chose a group for the ease of removal and for the ability to withstand the following reactions.

"Solution" as used herein is meant to encompass liquids wherein a reagent or reactant is present in a solvent in dissolved form (as a solute) or is present in particulate, undissolved form, or both. Thus, in a "solution", it is contemplated that the solute may not be entirely dissolved therein and solid solute may be present in dispersion or slurry form. Accordingly, a "solution" of a particular reagent or reactant is meant to encompasses slurries and dispersions, as well as solutions, of such reagents or reactants. "Solution" and "Slurry" may be used interchangeable herein.

"Solvent" as used herein is meant to encompass liquids that fully dissolve a reagent or reactant exposed to the solvent, as well as liquids which only partially dissolve the reagent or reactant or which act as dispersants for the reagent or reactant. Thus, when a particular reaction is carried out in a "solvent", it is contemplated that some or all of the reagents or reactants present may not be in dissolved form.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. A solvate may comprise differing ratios of number of molecules or moles of compound per molecule or mole of solvent present in the solvate. For example, a solvate may comprise a 1:1 relationship (mono-solvate), a 2:1 relationship (hemi-solvate), a 1:2 relationship (di-solvate, or the like, of compound to solvent.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as preferred, more preferred and most preferred definitions, if any.

"Treating" or "treatment" of a disease state includes:
(i) preventing the disease state, i.e. causing the clinical symptoms of the disease state not to develop in a subject that may be exposed to or predisposed to the disease state, but does not yet experience or display symptoms of the disease state.
(ii) inhibiting the disease state, i.e., arresting the development of the disease state or its clinical symptoms, or
(iii) relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Nomenclature and Structures

In general, the nomenclature used in this application is based on AUTONOM™ v.4.0, a Beilstein Institute computerized system for the generation of IUPAC systematic nomenclature. Chemical structures shown herein were prepared using ISIS® version 2.2. Any open valency appearing on a carbon, oxygen or nitrogen atom in the structures herein indicates the presence of a hydrogen atom. Where a chiral center is present in a structure but no specific stereochemistry is shown, both stereoisomers associated with the chiral center are encompassed by the structure.

Methods

U.S. patent application Ser. No. 11/315,706, filed on Dec. 21, 2005, published as US20060167255, and U.S. patent application Ser. No. 11/280,712 filed on Jun. 20, 2007, published as US20080015256, the disclosures of which are incorporated herein by reference, disclose compounds effective as modulators of the 5-HT$_6$ and 5-HT2$_a$ receptors and uses of these compounds for treatment of CNS diseases.

This invention provides methods useful for preparing such compounds, and chemical intermediates useful in such methods.

The methods of the invention will be more fully understood by first referring to Scheme A below, wherein:

R is $C_{1-6}$alkyl and may be the same or different in each occurrence;

X is a leaving group and may be the same or different in each occurrence;

m is 0 or 1;

n is from 0 to 3;

Ar is: aryl; or heteroaryl, each of which may be optionally substituted with: halo; $C_{1-6}$alkyl; $C_{1-6}$alkoxy; cyano; hydroxy; $C_{1-6}$alkylsulfonyl; or halo-$C_{1-6}$alkyl;

Y is —O—; —S(O)$_p$— or —N—R$^a$ wherein p is from 0 to 2 and R$^a$ is hydrogen or $C_{1-6}$alkyl;

D is an optionally chiral diamine;

E and E' are both halo, or E is hydrogen and E' is BH$_4$;

L is a chiral diphosphine ligand as described further below;

Z is: halo or R$^b$—CO$_2^-$ (carboxylate) wherein R$^b$ is: $C_{1-6}$alkyl; halo-$C_{1-6}$alkyl; $C_{1-6}$alkoxy; aryl optionally substituted with halo; or heteroaryl optionally substituted with halo;

R$^1$ is: halo; $C_{1-6}$alkyl; $C_{1-6}$alkoxy; or halo-$C_{1-6}$alkyl; and $R^2$ is —C(O)—$R^c$ or —$SO_2$—$R^c$ wherein $R^c$ is $C_{1-6}$alkyl or —$NR^dR^e$ wherein $R^d$ and $R^e$ each independently is hydrogen or $C_{1-6}$alkyl.
SCHEME A
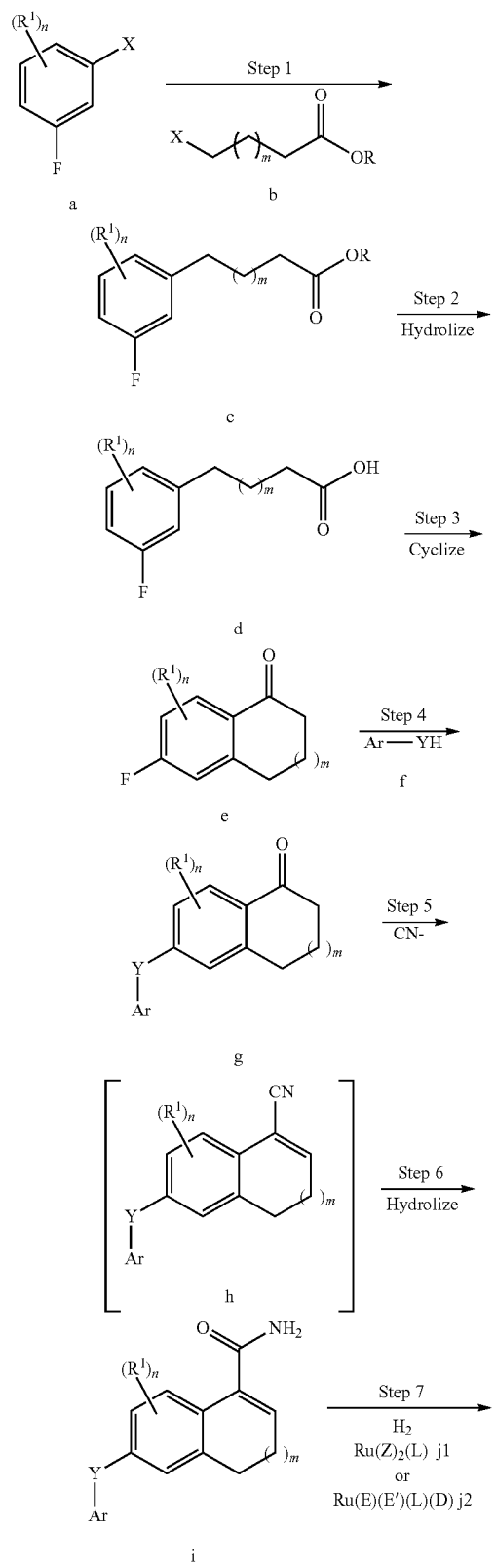
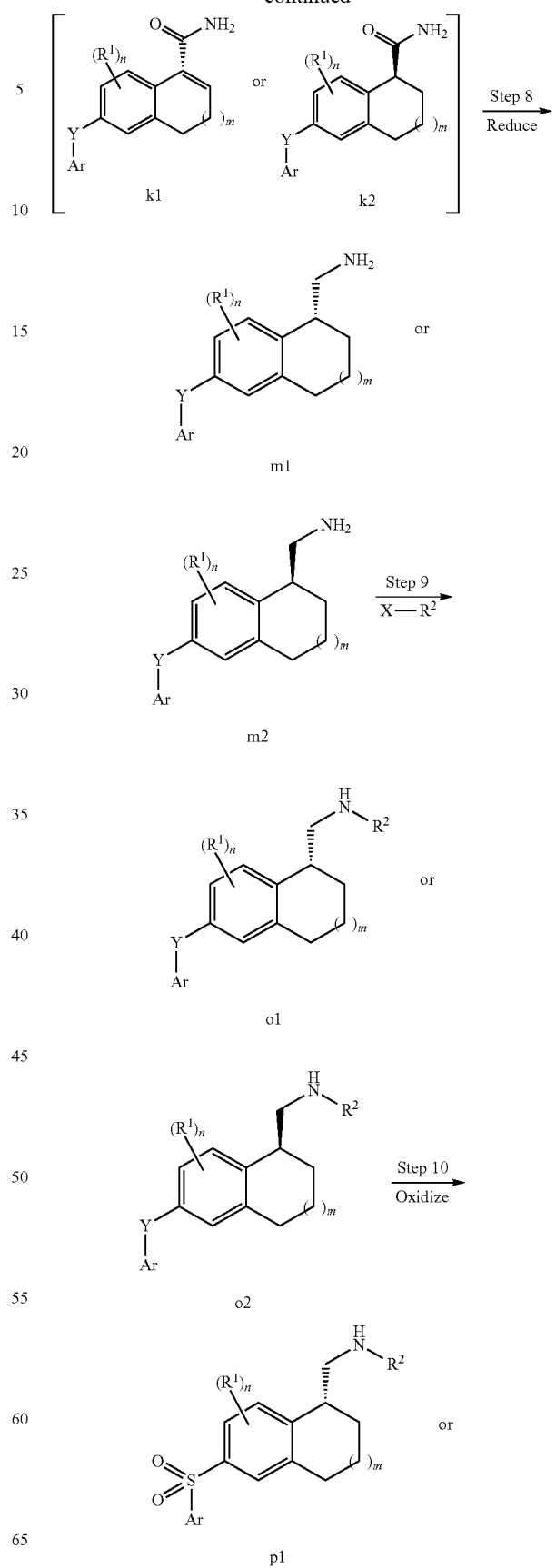

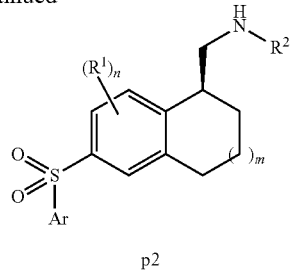

In step 1 of scheme A, fluorophenyl compound a is reacted with an ester compound b, to afford phenyl-alkyl carboxylic ester compound c. In embodiments where m=0, ester compound b is a propionate, and where m=1, compound b is a butyrate. R is preferably methyl or ethyl. The alkylation reaction of step 1 may be carried out, for example, under polar aprotic solvent conditions, such as in solution with NMP (N-methyl pyrrolidinone). The reaction may be carried out in the presence of zinc and iodine such that an intermediate zincate (not shown) compound is formed. The reaction may further be carried out in the presence of a phosphinylNi(II) catalyst such as bis(triphenylphosphine)Ni(II) chloride.

In step 2 the ester compound c undergoes hydrolysis to provide phenyl-alkyl carboxylic acid compound d. This hydrolysis may be carried out, for example, under aqueous conditions in the presence of base such as NaOH to form the corresponding carboxylate (not shown), which may then be treated with acid to give the corresponding carboxylic acid d.

A cyclization reaction is carried out in step 3 wherein compound d undergoes interal ring closure under aqueous acidic conditions to form a cyclicy ketone compound e. The reaction of step 3 may in many embodiments be effectively carried out in concentrated $H_2SO_4$. Where m=0, the cyclization of step 3 results in formation of an indane compound (not shown), and where m=1 results in formation of a tetralin compound as shown.

In step 4, tetralone compound e is reacted with nucleophilic aryl compound f to yield aryl substituted tetralone g. Compound f may comprise, for example, an aniline compound, a phenol compound or a thiophenol compound. The reaction of step 4 may be carried out under polar aprotic solvent conditions using NMP or a like solvent.

Cyclic ketone compound g is treated with cyanide in step 5 to give dihydronaphthalene carbonitrile compound h. The reaction of step 5 may be carried out in a non-polar solvent such as toluene. Trimethylsilyl cyanide (TMSCN) may be used as a cyanate source for step 5. This reaction may be carried out in the presence of $AlCl_3$. Carbonitrile compound h need not be isolated in certain embodiments, and thus compound h is shown in brackets.

In step 6, dihydronaphthalene carbonitrile compound h is hydrolyzed to form the corresponding dihydronaphthalene amide compound i. The hydrolysis may be achieved using sulfuric acid under aqueous conditions. As noted above, in certain embodiments nitrile compound h need not be isolated, and the events of steps 5 and 6 may occur in the same reaction vessel.

In step 7, dihydronaphthalene amide compound i is reduced, using either of chiral ruthenium catalysts j1 or j2, in the presence of hydrogen gas, to afford tetralin amide compound k1 or k2, depending on the configuration of catalyst j1 or j2. Several chiral ruthenium catalysts j1, j2 may be used in this step and are described in detail below. Use of (S) enantiomer catalyst j1 or j2 in the reduction of step 7 results primarily in (R) k1 as product, while use of (R) enantiomer catalyst j1 or j2 results primarily in (S) k2. In many embodiments an (S) enantiomer catalyst j1 or j2 is used to produce (R) enantiomer product k1.

One preferred catalyst j1 for preparing (R) enantiomer k1 is [Ru(OAc)$_2$(S)3,3'-Diphenyl-6,6'-dimethoxybiphenyl-2,2'-diyl)-bis-diphenylphosphine], also known as [Ru(OAc)$_2$(S)-MeOBIPHEP)]. The reduction of step 7 may be carried out using a polar aprotic solvent such as tetrahydrofuran (THF). In certain embodiments amide compound k1 or k2 does not require isolation, and step 8 may be carried out directly in the same reaction vessel used in step 6.

In step 8, a further reduction is carried out to convert chiral tetralin amide compound k1 or k2 to the corresponding chiral methylamino tetralin compound m1 or m2. The reduction of step 8 may be carried out, for example, using borane in a polar aprotic solvent such as THF. The configuration of compound k1 or k2 is preserved in the corresponding reduced product m1 or m2.

In step 9, aminomethyl tetralin compound m1 or m2 is treated with reagent n to afford tetralin compound o1 or o2. Reagent n may comprise, for example, an acyl halide such as acetyl chloride or other $C_{1-6}$-carboxylic acid chloride, a urea, an acyl anhydride such as acetic anhydride or other $C_{1-6}$-carboxylic acid anhydride, or a sulfonyl halide such as methanesulfonyl chloride. The reaction of step 9 may be carried out in solvents such as water or NMP. The configuration of compound m1 or m2 is preserved in the product compound o1 or o2.

In embodiments of the invention wherein Y is sulfur, an optional oxidation may be carried out in step 10 wherein compound o1 or o2 is treated with peracid, hydrogen peroxide, or like oxidizing agent to afford sulfonyl compound p1 or p2. The configuration of compound of o1 or o2 is preserved in the product compound p1 or p2.

Accordingly, the invention provides a method of producing a tetralin or indan amide of formula k1 or k2

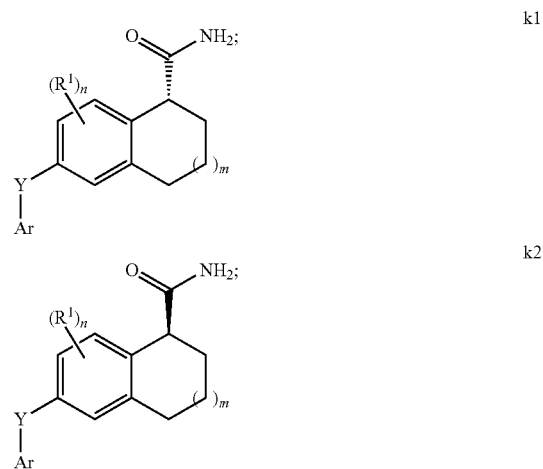

wherein:
m is 0 or 1;
n is from 0 to 3;
Ar is: aryl; or heteroaryl, each of which may be optionally substituted with: halo;
$C_{1-6}$alkyl; $C_{1-6}$alkoxy; cyano; hydroxy; $C_{1-6}$alkylsulfonyl; or halo-$C_{1-6}$alkyl;
Y is —O—; —S(O)$_p$— or —NR$^a$— wherein p is from 0 to 2 and R$^a$ is hydrogen or $C_{1-6}$alkyl; and $R^1$ is: halo; $C_{1-6}$alkyl; $C_{1-6}$alkoxy; or halo-$C_{1-6}$alkyl; the method comprising:

reducing a dihydronapthalene amide compound of formula i

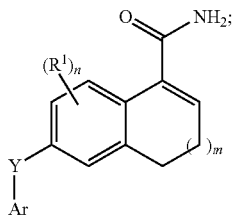

i with hydrogen gas in the presence of a Ruthenium catalyst of formula j1 or j2

$$Ru(Z)_2(L) \qquad j1;$$

$$Ru(E)(E')(L)(D) \qquad j2$$

wherein:
D is an optionally chiral diamine;
E and E' are both halo, or E is hydrogen and E' is $BH_4$;
L is a chiral diphosphine ligand; and
Z is: halo or $R^b$—$CO_2^-$ (carboxylate) wherein $R^b$ is: $C_{1-6}$alkyl; halo-$C_{1-6}$alkyl; $C_{1-6}$alkoxy; aryl optionally substituted with halo; or heteroaryl optionally substituted with halo.

In certain embodiments of the invention, m is 1.
In certain embodiments, m is 0.
In certain embodiments, n is 0 or 1.
In certain embodiments, n is 0.
In certain embodiments, n is 1.
In certain embodiments, Ar is phenyl optionally substituted with: halo; $C_{1-6}$alkyl; $C_{1-6}$alkoxy; cyano; hydroxy; $C_{1-6}$alkylsulfonyl; or halo-$C_{1-6}$alkyl.
In certain embodiments, Ar is phenyl optionally substituted with: fluoro; methyl; methoxy; cyano; hydroxy; methanesulfonyl; or trifluoromethyl.
In certain embodiments, Ar is phenyl optionally substituted with fluoro.
In certain embodiments, Ar is: heteroaryl selected from: indolyl; pyrrolyl; pyrazolyl; imidazolyl; and benzimidazolyl, each optionally substituted with halo, preferably fluoro.
In certain embodiments, Ar is: heteroaryl selected from: indol-3-yl; 5-fluoro-indol-3-yl; pyrrol-3-yl; 1-methyl-pyrrol-3-yl; pyrazol-4-yl; 1-methyl-imidazol-2-yl; and 5-fluoro-benzimidazol-7-yl.
In certain embodiments, Y is S.
In certain embodiments, Z is acetate ($CH_3COO^-$).
In certain embodiments, the catalyst is j1.
In certain embodiments, the catalyst is j2.
In certain embodiments, the chiral diphosphine L is selected from the group consisting of (R) or (S)-enantiomers of:
MeOBIPHEP;
(2-Furyl)-MeOBIPHEP)];
pTol-MeOBIPHEP;
3,5-Me,4-MeO-MeOBIPHEP;
3,5-iPr,4-MeO-MeOBIPHEP);
3,5-tBu-MeOBIPHEP;
3,5-tBu,4-MeO-MeOBIPHEP;
3,5-TMS-MeOBIPHEP;
TriMeOBIPHEP;
iPr-MeOBIPHEP;
Cy-MeOBIPHEP;
BenzoylOBIPHEP;
BITIANP;
BIPHEMP;
(2-Furyl)-BIPHEMP;
Et-Duphos;
BICP; and
PPF-P(tBu)$_2$).

In certain embodiments, the chiral diphosphine ligand L is an (R) or (S)-enantiomer of:
MeOBIPHEP;
BIPHEMP;
TMBTP;
2-Naphthyl)-MeOBIPHEP;
(6-MeO-2-Naphthyl)-MeOBIPHEP;
2-(Thienyl)-MeOBIPHEP;
3,5-tBu-MeOBIPHEP;
PHANEPHOS;
BICP;
TriMeOBIPHEP;
(R,R,S,S)-Mandyphos;
BnOBIPHEP;
BenzoylBIPHEP;
pTol-BIPHEMP;
tButylCOOBIPHEP;
iPrOBIPHEP;
p-Phenyl-MeOBIPHEP;
pAn-MeOBIPHEP;
pTol-MeOBIPHEP;
3,5-Xyl-MeOBIPHEP;
3,5-Xyl-BIPHEMP;
BINAP;
2-Furyl-MeOBIPHEP;
3,5-Xyl-4-MeO-MeOBIPHEP;
2-Furyl-MeOBIPHEP; and
BITIANP.

In certain embodiments, the chiral diphosphine ligand L is an (R) or (S)-enantiomer of MeOBIPHEP.
In certain embodiments, the chiral diphosphine L is (S)-MeOBIPHEP.\
In certain embodiments, the chiral diphosphine L is (R)-MeOBIPHEP.
In certain embodiments, L is (6,6'-Dimethoxybiphenyl-2,2'-diyl)bis-diphenylphosphine (MeOBIPHEP).
In certain enbodiments D is 1,2-bis-diphenyl-ethylenediamine (DPEN).
In certain embodiments, L is (S)-3,5-Xyl-MeOBIPHEP.
In certain embodiments, the catalyst is [Ru(OAc)$_2$((S)-MeOBIPHEP)] or [Ru(OAc)$_2$((R)-MeOBIPHEP)].
In certain embodiments, the catalyst is [Ru(OAc)$_2$((S)-MeOBIPHEP)].
In certain embodiments, the catalyst is [Ru(OAc)$_2$((R)-MeOBIPHEP)].
In certain embodiments, catalyst j1 is [Ru(OAc)$_2$((S)-(6,6'-Dimethoxy-biphenyl-2,2'-diyl)bis(diphenylphosphine))] and the tetralin amide compound of formula k1 is produced.
In certain embodiments, catalyst j2 is [Ru(OAc)$_2$((S)-3,5-Xyl-MeOBIPHEP)((R,R)-DPEN)] and the tetralin amide compound of formula k1 is produced.

The method of the invention further comprises:
reducing a compound of formula k1 or k2

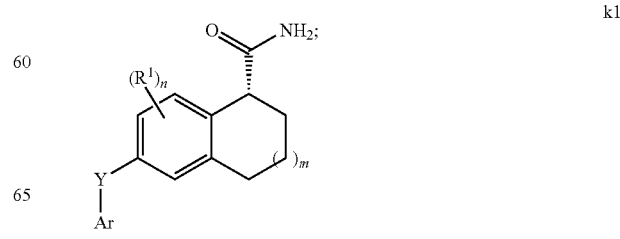

k1

-continued

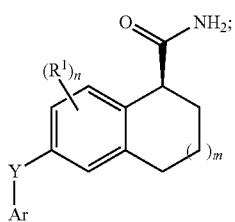

to provide a compound of formula m1 or m2

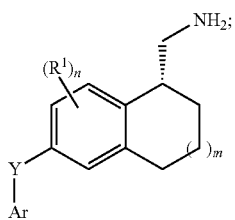
m1

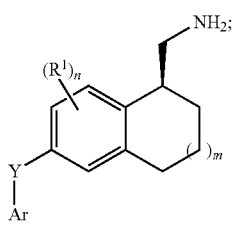
m2 wherein m, n, Y, Ar and $R^1$ are as defined herein.

In certain embodiments a compound of formula k1 is reduced to form a compound of formula m1.

In certain embodiments a compound of formula k2 is reduced to form a compound of formula m2.

In certain embodiments the reducing of the compound of formula k1 or k2 is carried out using borane.

The method of the invention may further comprise:
reacting a compound of formula m1 or m2

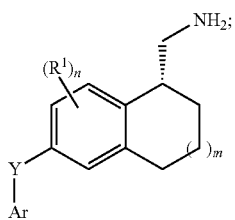
m1

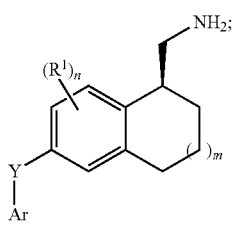
m2 with a reagent of formula n $$X—R^2$$
n;

to form a compound of formula o1 or o2

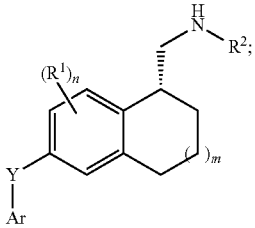
o1

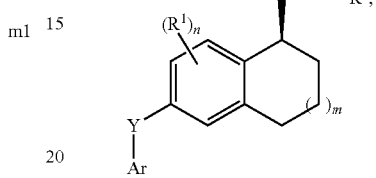
o2 wherein:
X is a leaving group;
$R^2$ is: —C(O)—$R^c$ or —SO$_2$—$R^c$ wherein $R^c$ is $C_{1-6}$alkyl or —NR$^d$R$^e$ wherein $R^d$ and $R^e$ each independently is hydrogen or $C_{1-6}$alkyl; and
m, n, Y, Ar and $R^1$ are as defined herein.

In certain embodiments a compound of formula m1 is reacted with a compound of formula n to form a compound of formula o1.

In certain embodiments a compound of formula m2 is reacted with a compound of formula n to form a compound of formula o2.

In certain embodiments the leaving group X is halo.

In certain embodiments the compound of formula n is acetyl chloride.

In certain embodiments the compound of formula n is urea.

In certain embodiments the compound of formula n is acetic anhydride.

In certain embodiments the compound of formula n is methanesulfonyl chloride.

The method may further comprise hydrolyzing/oxidizing a dihydronaphthalene carbonitrile compound h

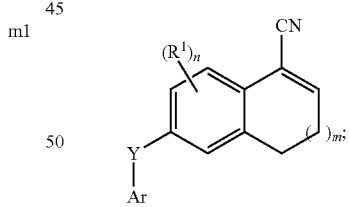
h to form the compound of formula i

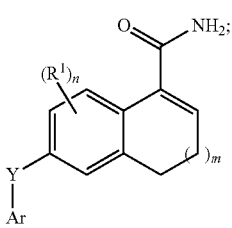
i wherein m, n, Y, Ar and $R^1$ are as defined herein.

In other embodiments the method may comprise treating a compound of formula g

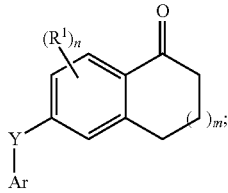

with cyanate, followed by treatment with sulfuric acid, to form the compound of formula i

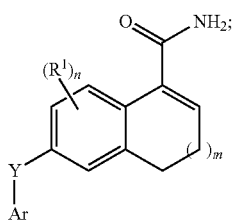

wherein m, n, Y, Ar and $R^1$ are as defined herein.

The method may further comprise reacting a compound of formula g

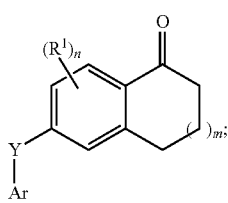

with cyanate, to afford the compound of formula h

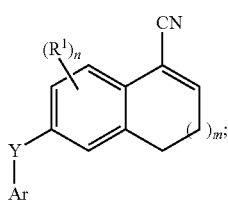

wherein m, n, Y, Ar and $R^1$ are as defined herein.

The method may further comprise reacting a compound of formula e

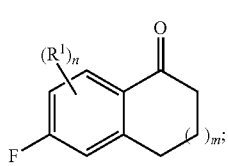

with a compound of formula f

Ar—YH  f;

to form the compound of formula g

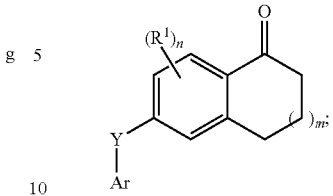

wherein m, n, Y, Ar and $R^1$ are as defined herein.

The method may further comprise cyclizing a compound of formula d

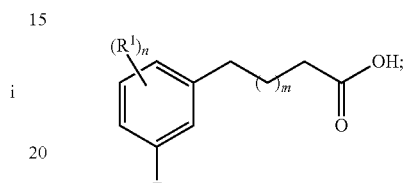

to form the compound of formula e.

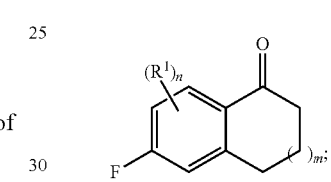

wherein m, n and $R^1$ are as defined herein.

The method may further comprise hydrolyzing a compound of formula c

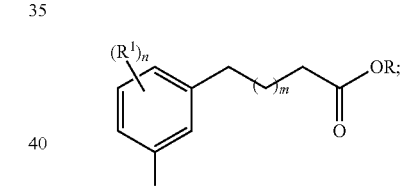

to form the compound of formula d

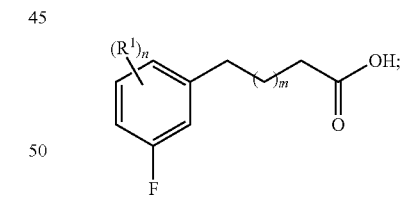

wherein m, n, R and $R^1$ are as defined herein.

The method may further comprise reacting a compound of formula a

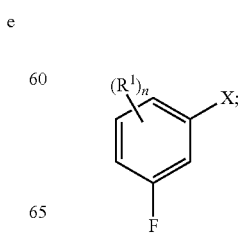

with a compound of formula b

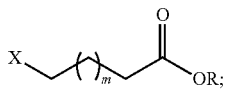

to form the compound of formula c

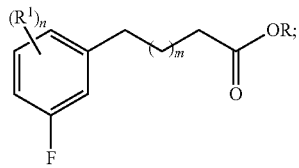

wherein m, n, X, R and R¹ are as defined herein.

The invention also provides a compound of formula k1 or k2

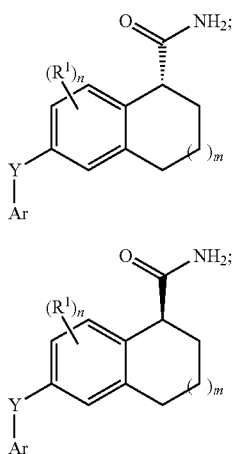

wherein:
m is 0 or 1;
n is from 0 to 3;
Ar is: aryl; or heteroaryl, each of which may be optionally substituted with: halo; $C_{1-6}$alkyl; $C_{1-6}$alkoxy; cyano; hydroxy; $C_{1-6}$alkylsulfonyl; or halo-$C_{1-6}$alkyl;
Y is —O—; —S(O)$_p$— or —N—R$^a$ wherein p is from 0 to 2 and R$^a$ is hydrogen or $C_{1-6}$alkyl; and
R¹ is: halo; $C_{1-6}$alkyl; $C_{1-6}$alkoxy; or halo-$C_{1-6}$alkyl.

The invention also provides a compound of formula i

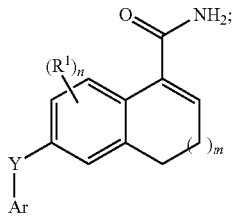

wherein:
m is 0 or 1;
n is from 0 to 3;
Ar is: aryl; or heteroaryl, each of which may be optionally substituted with: halo; $C_{1-6}$alkyl; $C_{1-6}$alkoxy; cyano; hydroxy; $C_{1-6}$alkylsulfonyl; or halo-$C_{1-6}$alkyl;
Y is —O—; —S(O)$_p$— or —N—R$^a$ wherein p is from 0 to 2 and R$^a$ is hydrogen or $C_{1-6}$alkyl; and
R¹ is: halo; $C_{1-6}$alkyl; $C_{1-6}$alkoxy; or halo-$C_{1-6}$alkyl.

Scheme B below illustrates a synthetic route to some preferred compounds of the invention, wherein:
X is a leaving group;
p is from 1 to 3;
R³ is: halo; $C_{1-6}$alkyl; $C_{1-6}$alkoxy; cyano; hydroxy; $C_{1-6}$alkylsulfonyl; or halo-$C_{1-6}$alkyl;
R$^f$ is $C_{1-6}$alkyl or —NR$^d$R$^e$ wherein R$^d$ and R$^e$ each independently is hydrogen or $C_{1-6}$alkyl; and
D, E, L, Z, n, R and R¹ are as defined herein.

SCHEME B

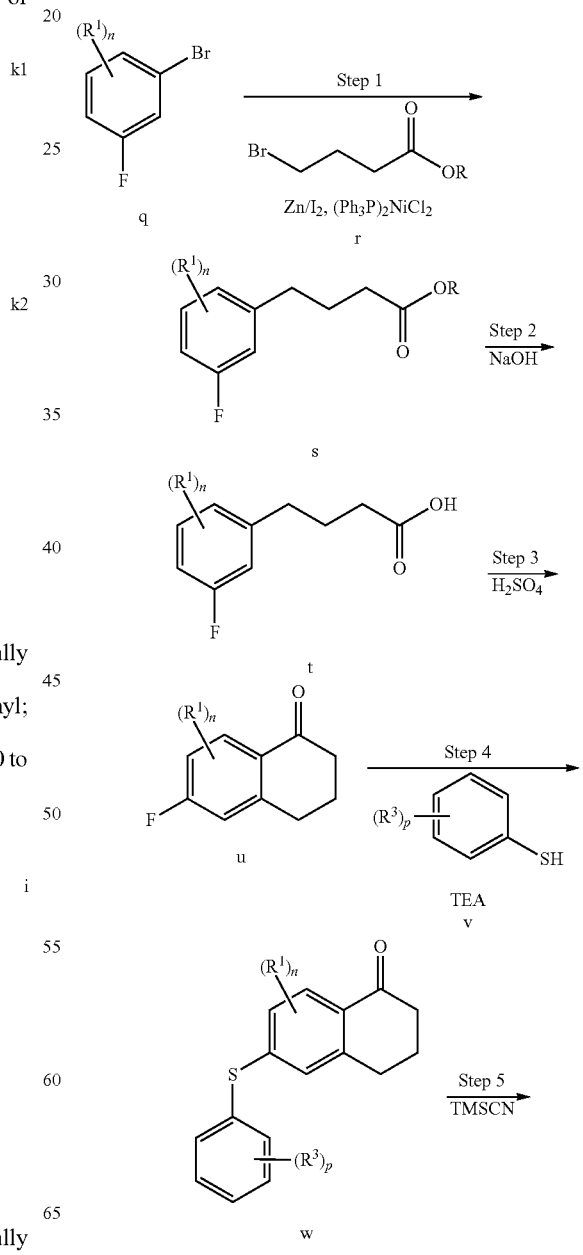

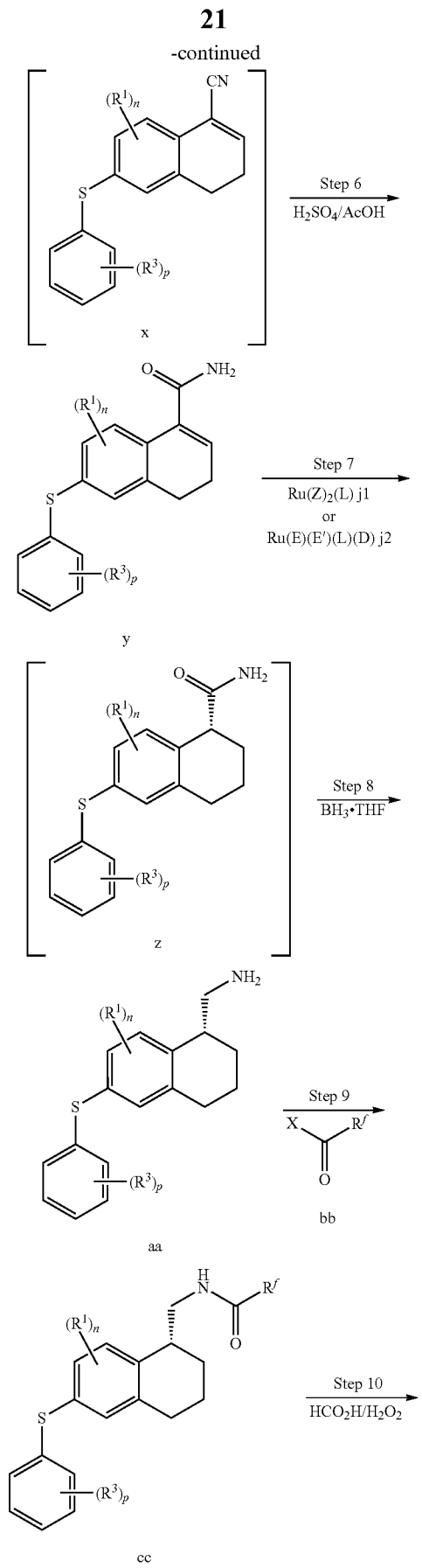

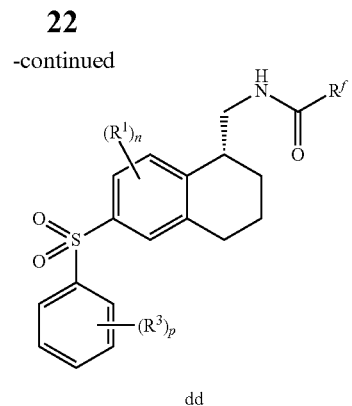

In step 1 of scheme B, bromofluorophenyl compound q is reacted with an gamma-bromo butyrate compound r, to afford gamma-phenyl butyrate compound s. This alkylation reaction may be carried out, for example, under polar aprotic solvent conditions, such as in solution with NMP (N-methylpyrrolidinone). The reaction is carried out in the presence of zinc and iodine such that an intermediate zincate (not shown) compound is formed. The reaction is further carried out in the presence of a phosphinylNi(II) catalyst such as bis(triphenylphosphine)Ni(II) chloride.

In step 2 butyrate compound s is hydrolyzed to afford phenyl-butyl carboxylic acid compound t. The hydrolysis may be carried out under aqueous conditions in the presence of NaOH to form the corresponding carboxylate (not shown), which is then be treated with acid to give the corresponding carboxylic acid t.

In step 3 a cyclization reaction is carried out in which carboxylic acid compound t undergoes interal ring closure under anhydrous or dehydrating conditions to form cyclic ketone compound u. The reaction of step 3 may in many embodiments be carried out in concentrated $H_2SO_4$.

In step 4, tetralone compound u is reacted with thiophenol compound v to yield phenyl sulfanyl cyclic ketone w. The reaction of step 4 may be carried out in the presence of an amine such as triethylamine, and under polar aprotic solvent conditions using NMP or a like solvent.

In step 5 cyclic ketone compound w is treated with trimethylsilyl cyanate to give dihydronaphthalene carbonitrile compound x. The reaction of step 5 may be carried out in a non-polar solvent such as toluene, and is preferably carried out in the presence of $AlCl_3$. Carbonitrile compound x need not be isolated in certain embodiments, and thus compound x is shown in brackets.

In step 6, dihydronaphthalene carbonitrile compound x is hydrolyzed to afford dihydronaphthalene amide compound y. Hydrolysis in this step may be achieved using sulfuric acid under aqueous conditions. As noted above, in certain embodiments nitrile compound x need not be isolated, and the events of steps 5 and 6 may occur in the same reaction vessel.

In step 7, dihydronaphthalene amide compound y is reduced, using chiral ruthenium catalyst j1 or j2 in the presence of hydrogen gas, to afford tetralin amide compound z. As noted above, several chiral ruthenium catalysts j1, j2 may be used for the asymmetric reduction of step 7. Use of (S) enantiomer catalyst j1 or j2 in the reduction of step 7 results primarily in (R) product z as shown. Use of (R) enantiomer catalyst j1 or j2 results primarily in the corresponding (R) isomer (not shown). A preferred catalyst j1 for preparing compound z is [Ru(OAc)$_2$((S)-6,6'-Dimethoxybiphenyl-2,2'-diyl)bis(diphenylphosphine)], also known as [Ru(OAc)$_2$((S)-MeO- BIPHEP)]. The reduction of step 7 may be carried out using a polar aprotic solvent such as tetrahydrofuran (THF).

In step 8, a further reduction is carried out to convert chiral tetralin amide compound z to the corresponding chiral methylamino tetralin compound aa. This reduction may be achieved using borane in a polar aprotic solvent such as THF. The configuration of compound z is preserved in the reduced product aa. The chiral amide compound z of step 7 need not be isolated in certain embodiments and may be reduced in situ in step 8.

In step 9, methylamino tetralin compound aa is treated with reagent bb to afford tetralin compound cc. Reagent bb may comprise, for example, an acyl halide such as acetyl chloride or other $C_{1-6}$-carboxylic acid chloride, a urea, or an acyl anhydride such as acetic anhydride or other $C_{1-6}$-carboxylic acid anhydride. The reaction of step 9 may be carried out in a polar aprotic solvent such as NMP. The configuration of compound aa is preserved in the product compound cc.

In step 10 compound cc is treated with peracid, hydrogen peroxide, or like oxidizing agent to afford sulfonyl compound dd. The configuration of compound cc is preserved in product compound dd.

Accordingly, the invention provides a method of producing a compound of formula z

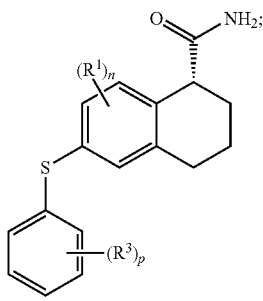

z wherein:
n is from 0 to 3;
p is from 1 to 3;
$R^1$ is: halo; $C_{1-6}$alkyl; $C_{1-6}$alkoxy; or halo-$C_{1-6}$alkyl; and
$R^3$ is: halo; $C_{1-6}$alkyl; $C_{1-6}$alkoxy; cyano; hydroxy; $C_{1-6}$alkylsulfonyl; or halo-$C_{1-6}$alkyl;
the method comprising:
reducing a compound of formula y

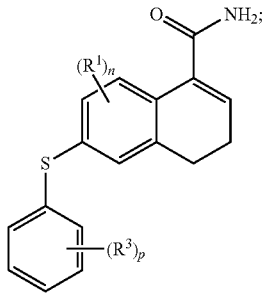

y with hydrogen gas in the presence of a catalyst of formula j1 or j2

Ru(Z)$_2$(L)      j1;

Ru(E)(E')(L)(D)      j2;

wherein:
D is an optionally chiral diamine;
E and E' are both halo, or E is hydrogen and E' is BH$_4$;
L is a chiral diphosphine ligand; and
Z is: halo or $R^b$—CO$_2^-$ (carboxylate) wherein $R^b$ is: $C_{1-6}$alkyl; halo-$C_{1-6}$alkyl; $C_{1-6}$alkoxy; aryl optionally substituted with halo; or heteroaryl optionally substituted with halo.

In certain embodiments, n is 0 or 1.
In certain embodiments, n is 0.
In certain embodiments, n is 1.
In certain embodiments, p is 0 or 1.
In certain embodiments, p is 0.
In certain embodiments, p is 1.
In certain embodiments, $R^1$ is: fluoro; methyl; methoxy; cyano; hydroxy; methanesulfonyl; or trifluoromethyl.
In certain embodiments, $R^1$ is fluoro.
In certain embodiments, $R^3$ is: fluoro; methyl; methoxy; cyano; hydroxy; methanesulfonyl; or trifluoromethyl.
In certain embodiments, $R^3$ is fluoro.
In certain embodiments, catalyst j1 is used.
In certain embodiments, catalyst j2 is used.
In certain embodiments, Z is acetate (CH$_3$COO$^-$).
In certain embodiments, the chiral diphosphine L is selected from the group consisting of (S)-enantiomers of:
MeOBIPHEP;
(2-Furyl)-MeOBIPHEP);
pTol-MeOBIPHEP;
3,5-Me,4-MeO-MeOBIPHEP;
3,5-iPr,4-MeO-MeOBIPHEP;
3,5-tBu-MeOBIPHEP;
3,5-tBu,4-MeO-MeOBIPHEP;
3,5-TMS-MeOBIPHEP;
TriMeOBIPHEP;
iPr-MeOBIPHEP;
Cy-MeOBIPHEP;
BenzoylOBIPHEP;
BITIANP;
BIPHEMP;
(2-Furyl)-BIPHEMP;
Et-Duphos;
BICP; and
PPF—P(tBu)$_2$.

In certain embodiments, the chiral diphosphine ligand L is an (R) or (S)-enantiomer of:
MeOBIPHEP;
BIPHEMP;
TMBTP;
2-Naphthyl)-MeOBIPHEP;
(6-MeO-2-Naphthyl)-MeOBIPHEP;
2-(Thienyl)-MeOBIPHEP;
3,5-tBu-MeOBIPHEP;
PHANEPHOS;
BICP;
TriMeOBIPHEP;
(R,R,S,S)-Mandyphos;
BnOBIPHEP;
BenzoylBIPHEP;
pTol-BIPHEMP;
tButylCOOBIPHEP;
iPrOBIPHEP;
p-Phenyl-MeOBIPHEP;
pAn-MeOBIPHEP;
pTol-MeOBIPHEP;
3,5-Xyl-MeOBIPHEP;
3,5-Xyl-BIPHEMP;
BINAP;
2-Furyl-MeOBIPHEP;

3,5-Xyl-4-MeO-MeOBIPHEP;

2-Furyl-MeOBIPHEP; and

BITIANP.

In certain embodiments, the chiral diphosphine ligand L is an (R) or (S)-enantiomer of MeOBIPHEP.

In certain embodiments, the chiral diphosphine L is (S)-MeOBIPHEP.\In certain embodiments, the chiral diphosphine L is (R)-MeOBIPHEP.

In certain embodiments, L is (S)-(6,6'-Dimethoxybiphenyl-2,2'-diyl)bisdiphenylphosphine.

In certain embodiments, L is (S)-3,5-Xyl-MeOBIPHEP.

In certain embodiments, the catalyst is [Ru(OAc)$_2$((S)-MeOBIPHEP)] or [Ru(OAc)$_2$((R)-MeOBIPHEP)].

In certain embodiments, the catalyst is [Ru(OAc)$_2$((S)-MeOBIPHEP)].

In certain embodiments, the catalyst is [Ru(OAc)$_2$((R)-MeOBIPHEP)].

In certain embodiments, catalyst j1 is [Ru(OAc)$_2$((S)-(6,6'-Dimethoxy-biphenyl-2,2'-diyl)bis(diphenylphosphine))].

In certain embodiments, catalyst j2 is [Ru(OAc)$_2$((S)-3,5-Xyl-MeOBIPHEP)((R,R)-DPEN)] and the tetralin amide compound of formula z is produced.

The method of the invention further comprises:

reducing a compound of formula z

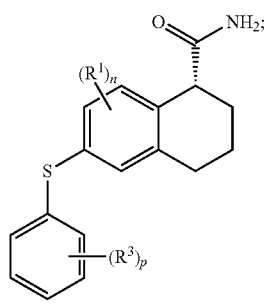

z to provide a compound of formula aa

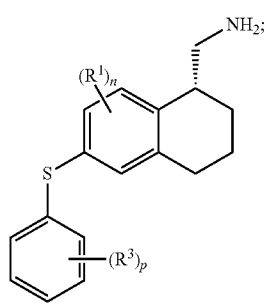

aa wherein n, p, R$^1$ and R$^3$ are as defined herein.

In certain embodiments the reducing of the compound of formula z is carried out using borane.

The method of the invention may further comprise:

reacting a compound of formula aa

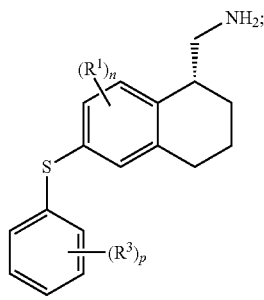

aa with a reagent of formula bb

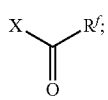

bb wherein:

X is a leaving group; and

R$^f$ is C$_{1-6}$alkyl or —NR$^d$R$^e$ wherein R$^d$ and R$^e$ each independently is hydrogen or C$_{1-6}$alkyl; and to form a compound of formula cc

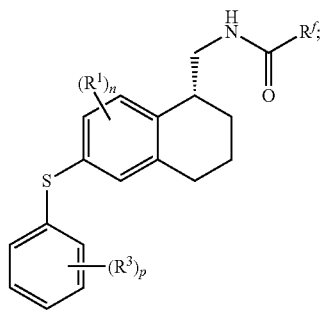

cc wherein n, p, R$^1$, R$^3$ and R$^f$ are as defined herein.

In certain embodiments the leaving group X is halo.

In certain embodiments the compound of formula bb is acetyl chloride.

In certain embodiments the compound of formula bb is urea.

In certain embodiments the compound of formula bb is acetic anhydride.

In certain embodiments R$^f$ is C$_{1-6}$alkyl.

In certain embodiments R$^f$ is NR$^d$R$^e$ wherein R$^d$ and R$^e$ each independently is hydrogen or C$_{1-6}$alkyl.

In certain embodiments R$^f$ is —NH$_2$.

In certain embodiments R$^f$ is methyl.

The method may further comprise:
oxidizing a compound of formula cc

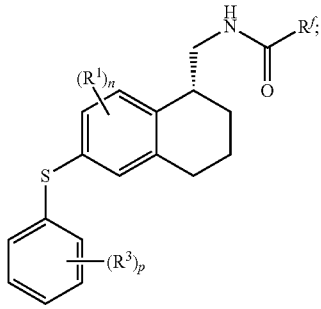

to form a compound of formula dd

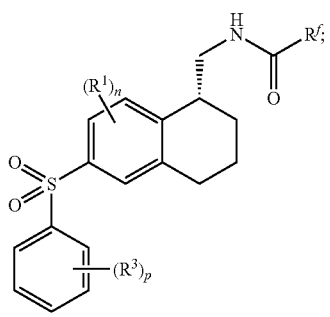

wherein n, p, R$^1$, R$^3$ and R$^f$ are as defined herein.

The method may further comprise oxidizing/hydrolyzing a dihydronaphthalene carbonitrile compound x

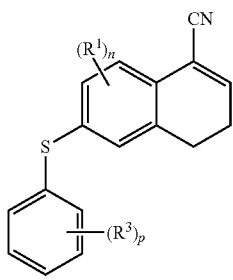

to form the compound of formula y

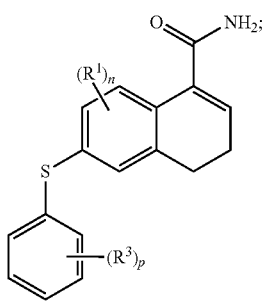

wherein n, p, R$^1$, and R$^3$ are as defined herein.

The method may further comprise reacting a compound of formula w

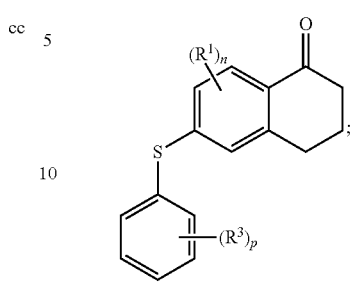

with trimethylsilyl cyanide, to afford the compound of formula x

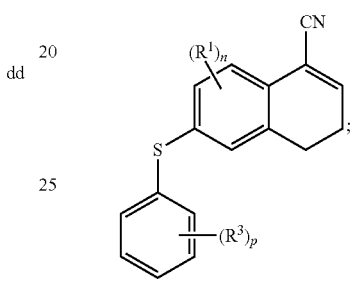

wherein n, p, R$^1$ and R$^2$ are as defined herein.

The method may further comprise reacting a compound of formula e

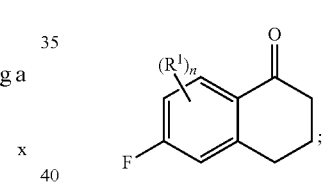

with a compound of formula v

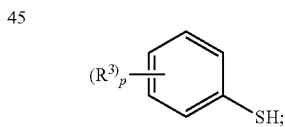

to form the compound of formula w

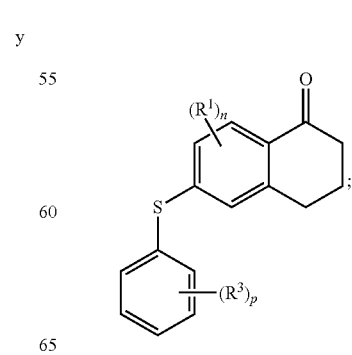

wherein n, p, R$^1$ and R$^2$ are as defined herein.

The method may further comprise cyclizing a compound of formula t

*[structure t: 3-fluorophenyl-(CH2)3-COOH with (R¹)ₙ]* to form the compound of formula u.

*[structure u: fluoro-tetralone with (R¹)ₙ]* wherein n and R¹ are as defined herein.

The method may further comprise hydrolyzing a compound of formula c

*[structure s: 3-fluorophenyl-(CH2)3-C(O)OR with (R¹)ₙ]* to form the compound of formula t

*[structure t: 3-fluorophenyl-(CH2)3-COOH with (R¹)ₙ]* wherein n, R and R¹ are as defined herein.

The method may further comprise reacting a compound of formula q

*[structure q: 3-bromo-fluorobenzene with (R¹)ₙ]* with a compound of formula r

*[structure r: Br-(CH2)3-C(O)OR]* to form the compound of formula s

*[structure s: 3-fluorophenyl-(CH2)3-C(O)OR with (R¹)ₙ]* wherein n, R and R¹ are as defined herein.

The invention also provides a compound of formula z

*[structure z: tetrahydronaphthalene-carboxamide with S-phenyl substituent, (R¹)ₙ and (R³)ₚ]* wherein:
n is from 0 to 3;
p is from 1 to 3;
R¹ is: halo; $C_{1-6}$alkyl; $C_{1-6}$alkoxy; or halo-$C_{1-6}$alkyl; and
R³ is: halo; $C_{1-6}$alkyl; $C_{1-6}$alkoxy; cyano; hydroxy; $C_{1-6}$alkylsulfonyl; or halo-$C_{1-6}$alkyl.

The invention also provides a compound of formula y

*[structure y: dihydronaphthalene-carboxamide with S-phenyl substituent, (R¹)ₙ and (R³)ₚ]* wherein:
n is from 0 to 3;
p is from 1 to 3;
R¹ is: halo; $C_{1-6}$alkyl; $C_{1-6}$alkoxy; or halo-$C_{1-6}$alkyl; and
R³ is: halo; $C_{1-6}$alkyl; $C_{1-6}$alkoxy; cyano; hydroxy; $C_{1-6}$alkylsulfonyl; or halo-$C_{1-6}$alkyl.

Specific details for the methods of the invention are described in the Examples section below.

Catalysts:

Ruthenium catalysts suitable for use with the methods of the invention may be represented by formula j $$\text{Ru}(Z)_2 L \quad \quad j1;$$

wherein:
Z is: halo; or $R^b$—$CO_2^-$ where $R^b$ is: $C_{1-6}$alkyl; halo-$C_{1-6}$alkyl; $C_{1-6}$alkoxy; aryl optionally substituted with halo; or heteroaryl optionally substituted with halo; and
L is a chiral diphosphine ligand.

The ruthenium complex catalysts are characterised by the oxidation number II. Such ruthenium complexes can optionally comprise further ligands, either neutral or anionic. Examples of such neutral ligands are e.g. olefins, e.g. ethylene, propylene, cyclooctene, 1,3-hexadiene, norbornadiene, 1,5-cyclooctadiene, benzene, hexamethylbenzene, 1,3,5-trimethylbenzene, p-cymene, or also solvents such as e.g. tetrahydrofuran, dimethylformamide, acetonitrile, benzonitrile, acetone and methanol. Examples of such anionic ligands are $CH_3COO^-$, $CF_3COO^-$ or halides. If the ruthenium complex is charged, non coordinating anions such as halides, $BF_4^-$, $ClO_4^-$, $SbF_6^-$, $PF_6^-$, $B(phenyl)_4^-$, $B(3,5-di-trifluoromethylphenyl)_4^-$, $CF_3SO_3^-$, $C_6H_5SO_3^-$ are present.

The ruthenium complex catalysts can be prepared, for example in the manner described by: N. Feiken et al., *Organometallics* 1997, 16, 537; M. P. Fleming et al., U.S. Pat. No. 6,545,165 (preparation and isolation of chiral ruthenium dicarboxylate diphosphine complexes); B. Heiser et al., *Tetrahedron: Asymmetry* 1991, 2, 51 (in-situ preparation of the same carboxylato complexes); or J.-P. Genet, *Acc. Chem. Res.* 2003, 36, 908, the disclosures of which are incorporated herein by reference. U.S. Pat. No. 6,545,165 in particular illustrates preparation of chiral ruthenium dicarboxylate diphosphines.

The ruthenium complex catalysts can be prepared in situ, i.e. just before use and without isolation. The solution in which such a catalyst is prepared can already contain the substrate for the enantioselective hydrogenation or the solution can be mixed with the substrate just before the hydrogenation reaction is initiated.

Surprisingly, it has been found that also ruthenium phosphine complexes of formula j2 may be used with the invention;

$$Ru(E)(E')(L)(D) \quad \quad j2$$

wherein E and E' are both halo or E is hydrogen and E' is $BH_4$; L is a chiral diphosphine ligand; and D is an optionally chiral diamine.

Complexes of type j2 can be specifically prepared, isolated and characterized in analogy to the methods described in *Angew. Chem. Int. Ed.* 1998, 37, 1703-1707 and in the references cited therein, or can be prepared "in situ" from components as described in above mentioned reference, and be employed without intermediate isolation in the catalytic asymmetric hydrogenation. When the complexes of type j2 are prepared "in situ", the amount of chiral diphosphine ligand (L) used in the reaction can vary from 0.5 to 2.5 equivalents relative to ruthenium, preferably from 0.8 to 1.2 equivalents. Analogously the amount of chiral diamine can vary from 0.5 to 2.5 equivalents based on the amount of the ruthenium-complex, preferably 1 to 2 equivalents.

The reaction may be carried out in presence of chiral diamines as depicted below;

V

DPEN

VI

DACH

VII

DTBEN

VIII

DABN

IX

DCEN

X

DAIPEN

Further suitable chiral diamines are propane- and butane-diamines. An especially preferred chiral diamine is DPEN (V), (R,R) or (S,S)-1,2-diphenyl-ethylenediamine. The chiral diamines are commercially available or can be prepared according to known methods.

In certain embodiments the chiral diphosphine ligand L of catalyst j1, j2 may be characterized by one of formulas (3), (4), (5), (6), (7), (8), (9), (10), (11), (12) or (13):

(3)

(4)
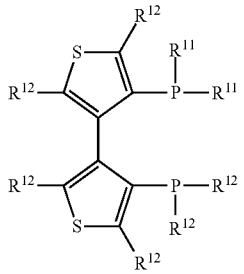

(5)
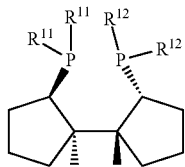

(6)
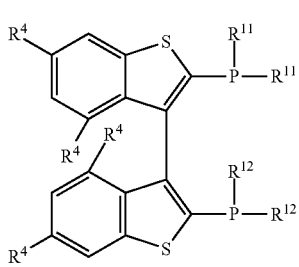

(3)
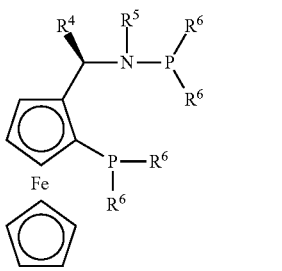

(10)
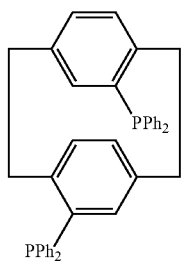

(11)

(12)

(13)

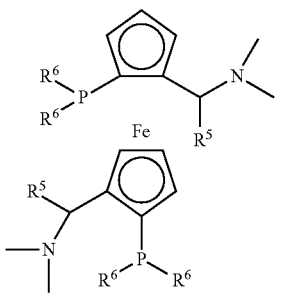

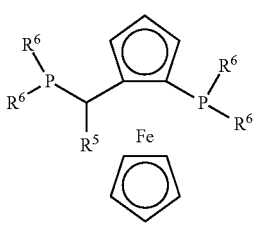

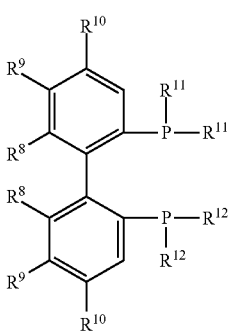

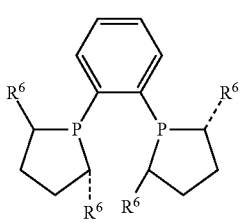

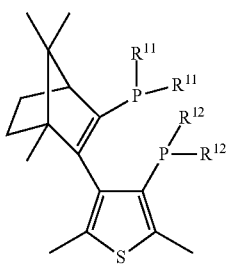

wherein
$R^4$ is $C_{1-6}$alkyl;
$R^5$ is $C_{1-6}$alkyl;
$R^6$ is independently in each occurrence aryl, heteroaryl, $C_{3-6}$cycloalkyl or $C_{1-6}$alkyl;
$R^7$ is —N($C_{1-6}$alkyl)$_2$ or piperidinyl;
$R^8$ is $C_{1-6}$alkyl, $C_{1-6}$alkoxy, hydroxy or $C_{1-6}$alkyl-C(O)O—; or the two $R^8$ substituents can be joined by a —O(CH$_2$)$_n$—O— bridge wherein n=2 to 5;
$R^9$ and $R^{10}$ independently are hydrogen, $C_{1-6}$alkyl, $C_{1-6}$alkoxy or di($C_{1-6}$alkyl)amino; or
$R^8$ and $R^9$ which are attached to the same phenyl group, or $R^9$ and $R^{10}$ which are attached to the same phenyl group, or both $R^8$, taken together, are -A-(CH$_2$)$_n$-E-, wherein A is —O— or —C(O)O—, E is —O— or —N($C_{1-6}$alkyl)- and n is an integer from 1 to 6, or a CF$_2$ group; or
$R^8$ and $R^9$, or $R^9$ and $R^{10}$, together with the carbon atoms to which they are attached, may form a naphthyl, tetrahydronaphthyl or dibenzofuran ring;
$R^{11}$ and $R^{12}$ each independently is $C_{1-6}$alkyl, $C_{3-6}$cycloalkyl, phenyl, napthyl or heteroaryl, substituted with 0 to 3 substituents independently selected from the group consisting of $C_{1-6}$alkyl, $C_{1-6}$alkoxy, di($C_{1-6}$alkyl)amino, morpholino, phenyl and tri($C_{1-6}$alkyl)silyl;

If R¹¹ is phenyl, it is substituted with 0 to 3 substituents as described above.

In certain embodiments, the chiral diphosphine ligand L is characterised by formula (7), (9), (10) or (12), and wherein Z is $CH_3COO$, $CF_3COO$ or a halogenide.

In certain embodiments, the chiral diphosphine L is selected from the group consisting of (R) or (S)-enantiomers of:
MeOBIPHEP;
(2-Furyl)-MeOBIPHEP);
pTol-MeOBIPHEP;
3,5-Me,4-MeO-MeOBIPHEP;
3,5-iPr,4-MeO-MeOBIPHEP;
3,5-tBu-MeOBIPHEP;
3,5-tBu,4-MeO-MeOBIPHEP;
3,5-TMS-MeOBIPHEP;
TriMeOBIPHEP;
iPr-MeOBIPHEP;
Cy-MeOBIPHEP;
BenzoylOBIPHEP;
BITIANP;
BIPHEMP;
(2-Furyl)-BIPHEMP;
(R,R)-Et-Duphos;
(all-S)-BICP; and
((S,R)-PPF-P(tBu)$_2$.
More preferably, the chiral diphosphine is selected from:
MeOBIPHEP;
pTol-MeOBIPHEP;
3,5-iPr,4-MeO-MeOBIPHEP; and
3,5-tBu,4-MeO-MeOBIPHEP
In certain embodiments, the chiral diphosphine ligand L is an (R) or (S)-enantiomer of:
MeOBIPHEP;
BIPHEMP;
TMBTP;
2-Naphthyl)-MeOBIPHEP;
(6-MeO-2-Naphthyl)-MeOBIPHEP;
2-(Thienyl)-MeOBIPHEP;
3,5-tBu-MeOBIPHEP;
PHANEPHOS;
BICP;
TriMeOBIPHEP;
(R,R,S,S)-Mandyphos;
BnOBIPHEP;
BenzoylBIPHEP;
pTol-BIPHEMP;
tButylCOOBIPHEP;
iPrOBIPHEP;
p-Phenyl-MeOBIPHEP;
pAn-MeOBIPHEP;
pTol-MeOBIPHEP;
3,5-Xyl-MeOBIPHEP;
3,5-Xyl-BIPHEMP;
BINAP;
2-Furyl-MeOBIPHEP;
3,5-Xyl-4-MeO-MeOBIPHEP;
2-Furyl-MeOBIPHEP; and
BITIANP.

In certain embodiments, the chiral diphosphine ligand L is an (R) or (S)-enantiomer of MeOBIPHEP.

In certain embodiments, the chiral diphosphine L is (S)-MeOBIPHEP.\

In certain embodiments, the chiral diphosphine L is (R)-MeOBIPHEP.

In certain embodiments, L is (S)-3,5-Xyl-MeOBIPHEP.

In certain embodiments, the catalyst is [Ru(OAc)$_2$((S)-MeOBIPHEP)] or [Ru(OAc)$_2$((R)-MeOBIPHEP)].

In certain embodiments, the catalyst is [Ru(OAc)$_2$((S)-MeOBIPHEP)].

In certain embodiments, the catalyst is [Ru(OAc)$_2$((R)-MeOBIPHEP)].

Definitions for the above abbreviations used for ligands, as well as literature and commercial sources, are provided in Table 1 below.

TABLE 1

TABLE 1
LIGANDS IN THE EXAMPLES

| | | |
|---|---|---|
| 1) MeOBIPHEP | (6,6'-Dimethoxybiphenyl-2,2'-diyl)bis(diphenylphosphine) (prepared as described in EP 0 398 132, WO 92/16535, EP 0 104 375 or EP 0 580 331) |
| 2) 2-Furyl-MeOBIPHEP | (6,6'-Dimethoxybiphenyl-2,2'-diyl)bis(di-2-furylphosphine) (prepared as described in EP 0 398 132, WO 92/16535, EP 0 104 375 or EP 0 580 331) |
| 3) pTol-MeOBIPHEP | (6,6'-Dimethoxybiphenyl-2,2'-diyl)bis[di(p-tolyl)phosphine] (prepared as described in EP 0 398 132, WO 92/16535, EP 0 104 375 or EP 0 580 331) |
| 4) 3,5-Me,4-MeO-MeOBIPHEP | (6,6'-Dimethoxy[1,1'-biphenyl]-2,2'-diyl)bis[bis(3,5-di-tert-butyl-4-methoxyphenyl)phosphine) (prepared as described in EP 0 398 132, WO 92/16535, EP 0 104 375 or EP 0 580 331) |
| 5) 3,5-ipr,4-MeO-MeOBIPHEP | (6,6'-Dimethoxy[1,1'-biphenyl]-2,2'-diyl)bis[bis(3,5-di-iso-propyl-4-methoxyphenyl)phosphine) |
| 6) 3,5-tBu-MeOBIPHEP | (6,6'-Dimethoxy[1,1'-biphenyl]-2,2'-diyl)bis[bis(3,5-di-tert-butyl-phenyl)phosphine) (prepared as described in EP 0 398 132, WO 92/16535, EP 0 104 375 or EP 0 580 331) |
| 7) 3,5-tBu,4-MeO-MeOBIPHEP | (6,6'-Dimethoxy[1,1'-biphenyl]-2,2'-diyl)bis[bis(3,5-di-tert-butyl-4-methoxyphenyl)phosphine) |
| 8) 3,5-TMS-MeOBIPHEP | (6,6'-Dimethoxy[1,1'-biphenyl]-2,2'-diyl)bis[bis(3,5-bis-trimethylsilyl-phenyl)phosphine) |
| 9) TriMeOBIPHEP | Phosphine, (4,4',5,5',6,6'-hexamethoxy[1,1'-biphenyl]-2,2'-diyl)bis[diphenyl] (prepared as described in EP 0 398 132, WO 92/16535, EP 0 104 375 or EP 0 580 331) |
| 10) iPr-MeOBIPHEP | 2,2-Bis-(diisopropylphosphino)-6,6-dimethoxy-1,1'-biphenyl (preparation described in Schmid et al., *Pure and Applied Chemistry* 1996, 68(1), 131-8) and in Foricher et al. PCT Int. Appl. (1993), WO 9315091 A1) |

TABLE 1-continued
LIGANDS IN THE EXAMPLES

| | | |
|---|---|---|
| 11) Cy-MeOBIPHEP | (2,2-Bis-(dicyclohexylphosphino)-6,6-dimethoxy-1,1'-biphenyl (preparation described in Schmid et al., *Pure and Applied Chemistry* 1996, 68(1), 131-8) and in Foricher et al. PCT Int. Appl. (1993), WO 9315091 A1) | |
| 12) BenzoylBIPHEP | (6,6'-Dibenzoyloxybiphenyl-2,2'-diyl)bis(diphenylphosphine) (Prepared as described in WO 2002012253) | |
| 13) BITIANP | 3,3'-bis-diphenylphosphanyl-1H,1'H-[4,4']-biisothiochromenyl (prepared as described by Benincori, T.; Brenna, E.; Sannicolo, F.; Trimarco, L.; Antognazza, P.; Cesarotti, E.; Demartin, F.; Pilati, T. *J. Org. Chem.* 1996, 61, 6244) | |
| 14) BIPHEMP | (6,6'-Dimethylbiphenyl-2,2'-diyl)bis(diphenylphosphine) (prepared as described in EP 0 398 132, WO 92/16535, EP 0 104 375 or EP 0 580 331) | |
| 15) (2-Furyl)-BIPHEMP) | (6,6'-Dimethylbiphenyl-2,2'-diyl)bis(di-2-furylphosphine) (prepared as described in EP 0 398 132, WO 92/16535, EP 0 104 375 or EP 0 580 331) | |
| 16) Et-Duphos | 1,2-Bis((2,5-diethylphospholano)benzene Commercially available from Sigma-Aldrich, P O Box 14508, St. Louis, MO, 63178, USA | |
| 17) BICP | 2,2'-bis(diphenylphosphino)-(1S,1'S,2S,2'S)-1,1'-bicyclopentyl (Commercially available from Chiral Quest Inc., Princeton Corporate Plaza, Monmouth Jct., NJ 08852, USA) | |
| 18) PPF-P(tBu)$_2$ | 1-[(2-Diphenylphosphino)ferrocenyl]ethyldi-tert.-butyl-phosphine (Commercially available from Solvias AG Basel Switzerland) | |

The hydrogenation is preferably carried out in an organic solvent which is inert under the reaction conditions. As such solvents there can be mentioned, in particular, lower alcohols such as e.g. methanol, ethanol or isopropanol, trifluoroethanol, ethers such as e.g. diethyl ether, tetrahydrofuran or dioxane, or mixtures of such alcohols with halogenated hydrocarbons such as methylene chloride, chloroform, hexafluorobenzene and the like or with ethers such as diethyl ether, tetrahydrofuran or dioxane. Preferred solvents for the reaction are lower alcohols, especially preferred is methanol, or ethers, especially preferred is tetrahydrofuran. The reaction is carried out at a concentration of about 1 to 50%, ideally about 5 to 30%

The substrate/catalyst ratio (S/C ratio) is 100-100,000, preferably 500-30,000. The hydrogenation is carried out at a pressure of 1 to 300 bar, ideally at a pressure of about 1 to 50 bar and at a temperature of about 0° C. to about 150° C., ideally at 20° C. to 100° C.

The asymmetric hydrogenations can be carried out either batchwise or in a continuous manner.

Utility

The methods and compounds of the invention are useful for preparation of compounds that in turn are usable for the treatment of central nervous system diseases, conditions and disorders, including Parkinson's disease, Huntington's disease, anxiety, depression, manic depression, psychosis, epilepsy, obsessive compulsive disorders, mood disorders, migraine, Alzheimer's disease (enhancement of cognitive memory), sleep disorders, feeding disorders such as anorexia, bulimia, and obesity, panic attacks, akathisia, attention deficit hyperactivity disorder (ADHD), attention deficit disorder (ADD), withdrawal from drug abuse such as cocaine, ethanol, nicotine and benzodiazepines, schizophrenia, and also disorders associated with spinal trauma and/or head injury such as hydrocephalus. The methods are particularly useful for preparation of compounds for treatment of memory disorders, for enhancing cognition, and for enhancing cognition in Alzheimer's patients.

EXAMPLES

The following examples are given to enable those skilled in the art to more clearly understand and to practice the present invention. They should not be considered as limiting the scope of the invention, but merely as being illustrative and representative thereof. The following abbreviations may be used in the Examples.

ABBREVIATIONS

HPLC high pressure liquid chromatography
DABN 2,2'-Diamino-1,1'-binaphthalene
DACH trans-1,2-Diaminocyclohex an
DAIPEN 1,1-Di(p-methoxyphenyl)-2-isopropylethyl-enedi amine
DCEN 1,2-Dicyclohexane-ethylendiamine
DCM dichloromethane/methylene chloride
DMF N,N-dimethylformamide
DMAP 4-dimethylaminopyridine
DTBEN 1,2-Di-tert.-butylethylenediamine
EtOAc ethyl acetate
EtOH ethanol
Et$_2$O diethyl ether
GC gas chromatography
HMPA hexamethylphosphoramide
hplc high performance liquid chromatography
IPA isopropanol
mCPBA m-chloroperbenzoic acid
MeCN acetonitrile
MeOH methanol
MTBE methyl tert-butyl ether
NMP N-methylpyrrolidinone
TEA triethylamine
THF tetrahydrofuran
LDA lithium diisopropylamine
TLC thin layer chromatography
TMSCN trimethylsilyl cyanate
S/C Substrate-to-catalyst molar ratio
DPEN 1,2-Diphenyl-ethylenediamine

Example 1
[(R)-6-(3-Fluoro-phenylsulfonyl)-1,2,3,4-tetrahydro-naphthalen-1-ylmethyl]-urea
The synthetic procedure used in this Example is outlined in Scheme C.
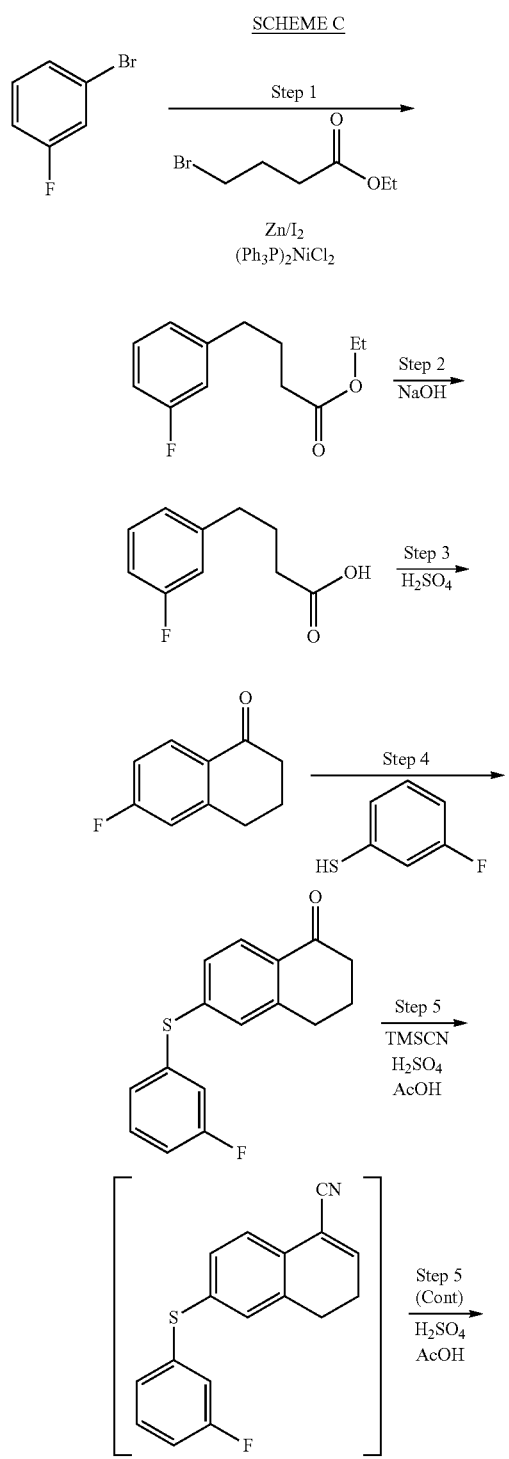
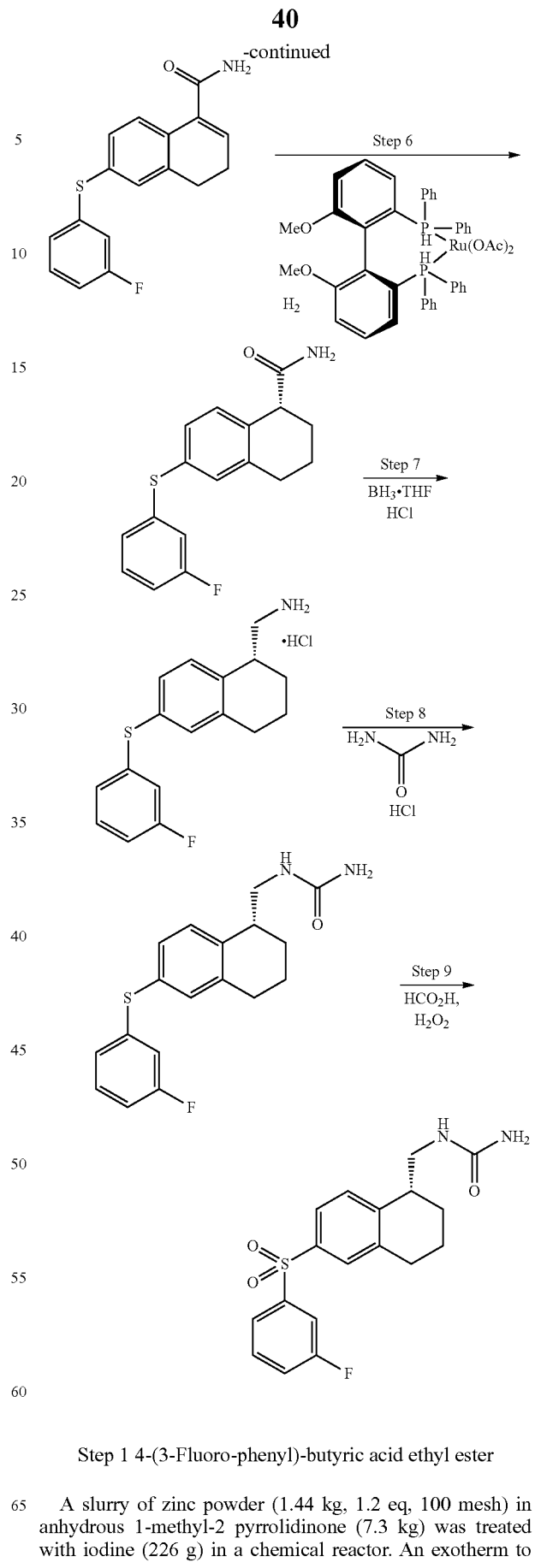
Step 1 4-(3-Fluoro-phenyl)-butyric acid ethyl ester
A slurry of zinc powder (1.44 kg, 1.2 eq, 100 mesh) in anhydrous 1-methyl-2 pyrrolidinone (7.3 kg) was treated with iodine (226 g) in a chemical reactor. An exotherm to about 40° C. occurred and the iodine color disappeared. With good agitation the temperature was raised to about 60° C. and ethyl 4-bromobutyrate (4.2 kg) was charged while monitoring for an exotherm above the reactor jacket temperature. The reaction was initiated by adding one kg of ethyl 4-bromobutyrate and heating the jacket to about 55° C. Reaction onset was detected at about 55° C. The reaction temperature was controlled incrementally from 60 to about 95° C. by slow addition of the remaining 3.2 kg of ethyl 4-bromobutyrate. At the end of the addition the reaction mixture was heated to about 95° C. until the reaction was complete (approximately 2% starting material by GC). Formation of the intermediate zincate (not shown in Scheme C) was confirmed by GC analysis, (a sample aliquot was quenched into 4N hydrochloric acid and extracted with MTBE). The reaction mixture was cooled to about 25° C. and bis(triphenylphosphine)nickel(II) chloride 45.8 g added. The reaction mixture was then heated to about 40° C. and 1-bromo-3-fluorobenzene (3.23 kg) was added over a period of about 6 hours. The reaction temperature was maintained between 35 and 45° C. by controlling the addition rate of 1-bromo-3-fluorobenzene. The exotherm was monitored by the temperature differential between the jacket and the reactor internal probe. Once the addition was complete the reaction mixture was heated for 24 hours at 40° C. The reaction was cooled to 15° C. and quenched with water (4.5 liters), acidified with 6N aqueous hydrochloric acid (14 liters) and stirred until all gas evolution had ceased and all salts had dissolved. The crude reaction mixture was filtered through a bed of celite. The celite bed was washed through with MTBE (10 liters) and charged to an extractor ball. The extractor ball was charged with additional fresh MTBE (5 liters) and the filtered aqueous reaction mixture was extracted in portions and split off. The organic layer in the extractor ball was washed with three times with water (5 liters each time). The organic layer was separated and concentrated in vacuo and the resulting crude 4-(3-fluoro-phenyl)-butyric acid ethyl ester (10.5-kg), isolated as an oil, was used without further purification in the next step: MS (M+1)=210; $H^1$ NMR (300 MHz): δ ppm (CDCl$_3$): 1.25 (3H, t, J=7.16 Hz), 1.94 (2H, dp), 2.31 (2H, t, J=7.54 Hz), 2.65 (2H, t, J=7.54 Hz), 4.12 (2H, q, J=7.16), 6.84-6.96 (2H, m), 7.19-7.26 (2H, m).

Step 2 4-(3-Fluoro-phenyl)-butyric acid

Crude 4-(3-fluorophenyl)butyric acid ethyl ester (10.5-kg), water (15.8 L) and 50% NaOH (12.0 kg) were charged to a reactor and stirred at 50° C. for 2 hours. The hydrolysis generated a mild exotherm to 55° C. The biphasic mixture became monophasic. Completion of the hydrolysis was confirmed by LC. The reaction mixture was cooled to 20° C. and washed with hexanes 15 kg (containing antistatic agent "ASA 3") to remove 3'3-difluorobiphenyl impurity generated in the previous step. After phase separation the aqueous layer was acidified with 37% concentrated HCl (16.7 kg), keeping the exotherm below 40° C. Upon cooling the aqueous layer was extracted with MTBE (15 kg in three 5 kg extractions). The solvent was removed by vacuum distillation and excess MTBE removed with a hexane strip. The resulting 4-(3-fluoro-phenyl)-butyric acid (8.83 kg) was removed from the reactor as an oil and used without further purification: MS (M+1)=182; $H^1$ NMR (300 MHz): δ ppm (CDCl$_3$): 1.965 (2H, p, J=4.9, 2.47 hz), 2.37 (2H, t, J=2.47 Hz), 2.66 (2H, t, J=2.45), 6.87 (2H, m), 6.95 (1H, d, J=2.63), 7.22 (1H, m) 11.2 (0.2H, bs).

Step 3 6-Fluoro-3,4-dihydro-2H-naphthalen-1-one

Crude 4-(3-fluorophenyl)butyric acid (8.83 kg) was added to concentrated sulfuric acid (30 kg) in a chemical reactor at a rate such that the pot temperature stayed between 40° C. and 60° C. (jacket heating was not necessary). The reaction was stirred at 45° C. for 3 hours and reaction completion was confirmed by LC. The reaction mixture was cooled and quenched with water (16 L), and then extracted with 35% THF in methylene chloride (25.8 kg). The organic layer was separated and washed with water (16 L), saturated aqueous NaHCO$_3$ (16.9 kg) and then a mixture of water (16.1-kg)/brine (4.7-kg). The organic later was concentrated under vacuum and re-stripped with the aid of hexane to remove water and afford 6-fluoro-3,4-dihydro-2H-naphthalen-1-one as an oil (5.88 kg): MS (M+1)=165; $H^1$ NMR (300 MHz): δ ppm (CDCl$_3$): 2.14 (2H, m, J=6.03, 5.75 Hz), 2.64 (2H, dd, J=6.03, 5.75 Hz); 2.94 (2H, t, J=6.03), 6.9-7.0 (2H, m, J=2.26, 2.64, 6.03 Hz), 8.02-8.07 (1H, dd, J=6.03).

Step 4 6-(3-Fluoro-phenylsulfanyl)-3,4-dihydro-2H-naphthalen-1-one

A solution of 6-fluoro-3,4-dihydro-2H-naphthalen-1-one (3.64 kg) and 3-fluorothiophenol (2.80 kg), in anhydrous NMP (7.7 kg) was treated with triethylamine (2.26 kg). After a mild exotherm had subsided, the mixture was heated for 20 hours at 90° C. The mixture was cooled to about 25° C. and diluted with water (30 L) and heptane (10 kg). The mixture was agitated for 12 hours and then filtered. The filter cake was washed with water and dried at 60° C. under vacuum to afford 6-(3-fluorophenylsulfanyl)-3,4-dihydro-2H-naphthalen-1-one (5.52 kg): MP=66.2-66.7° C.; MS (M+1)=273; $H^1$ NMR (300 MHz): δ ppm (CDCl$_3$): 2.10 (2H, m, J=6.03, 6.40 Hz), 2.62 (2H, dd, J=6.03, 5.75 Hz) 2.87 (2H, t, J=6.03), 7.03 (1H, tdd, J=1.13, 2.64, 8.29 Hz), 7.08-7.16 (2H, m), 7.22 (1H, dt, J=1.13, 8.29 Hz), 7.31 (1H, q, 8.29 Hz), 7.35 (1H, dd, J=5.65, 7.91 Hz) 7.92 (1H, d, J=7.91 Hz).

Step 5 6-(3-Fluoro-phenylsulfanyl)-3,4-dihydro-naphthalene-1-carboxylic acid amide 6-(3-Fluoro-phenylsulfanyl)-3,4-dihydro-2H-naphthalene-1-one (4.78 kg) was dissolved in toluene (50 kg) and the resulting mixture was azeotropically distilled under vacuum at 50 to 55° C. until approximately 10 L of toluene remained. The solution was cooled to 25° C. and AlCl$_3$ (52 g) was added. TMSCN (1.85 kg) was added at a rate such that the reaction temperature was kept between 20 and 50° C. The reaction was monitored for completion by TLC (Hexanes/EtOAc 4:1). The resulting 6-(3-Fluoro-phenylsulfanyl)-3,4-dihydro-naphthalene-1-carbonitrile was not isolated from the reaction mixture. Once complete the reaction was cooled to 5° C. and sulfuric acid (4.06 kg) was added slowly to maintain an internal temperature below 30° C. The reaction was then diluted with acetic acid (24 kg), sulfuric acid (18 kg) and water (2.4 kg). The reaction mixture was heated to 105° C. for three hours, then cooled to 25° C. and quenched with water (48 kg). The product was filtered and washed thoroughly with water (28 kg), MTBE (10.6 kg), and dried under vacuum with a nitrogen purge to afford 6-(3-fluoro-phenylsulfanyl)-3,4-dihydro-naphthalene-1-carboxylic acid amide as a white solid (4.59-kg): MP=167.9-169.7° C.; MS (M+1)=300; $H^1$ NMR (300 MHz): δ ppm (DMSO): 2.31 (2H, m, J=4.29, 8.29 Hz), 2.72 (1H, t, J=7.91), 3.64 (0.5H, s, NH), 6.54 (1H, t, J=4.52 Hz), 7.02-7.12 (3H, m), 7.22 (~0.5H, bs, NH), 7.25-7.30 (2H, m), 7.35-7.42 (2H, m), 7.52 (1H, d, J=8.67), 7.67 (1H, bs, NH).

Step 6 (R)-6-(3-Fluoro-phenylsulfanyl)-1,2,3,4-tetrahydro-naphthalene-1-carboxylic acid amide A suspension of 6-(3-fluorophenylsulfanyl)-3,4-dihydronaphthalene-1-carboxylic acid amide (2.3 kg) and [Ru (OAc)$_2$((S)-MeOBIPHEP)] (1.36 g) in THF (25 kg) was hydrogenated at 40° C. and 160 psi (11 bar) of hydrogen for 36 hours to afford a solution of (R)-6-(3-fluoro-phenylsulfanyl)-1,2,3,4-tetrahydro-naphthalene-1-carboxylic acid amide in THF that was used directly in the next step. Analysis of an aliquot of the THF solution provided the following data:

MP=131.9-132.6° C.; MS (M+1)=302 H$^1$ NMR (300 MHz): δ ppm (DMSO): 1.61 (1H, m), 1.92 (2H, m), 2.70 (2H, m), 3.63 (1H, t, J=6.78 Hz), 6.97-7.10 (4H, m), 7.13-7.22 (3H, m), 7.33-7.40 (1H, m), 7.50 (1H, NH); [α]$_D$=4.0° (MeOH). Chiral Assay (Area Norm): Column: ChiralCel OD-H (250×4.6 mm), mobile phase 90/10 hexane/ethanol (isocratic), flow rate 0.7 ml/min, 25° C., uv @230 nm.: (R)-isomer 98.59/(S)-isomer 1.41.

Step 7 [(R)-6-(3-Fluoro-phenylsulfanyl)-1,2,3,4-tetrahydro-naphthalen-1-yl]-methylamine hydrochloride A solution of (R)-6-(3-fluorophenylsulfanyl)-1,2,3,4-tetrahydronaphthalene-1-carboxylic acid amide (approximately 4.63 kg) in THF was concentrated to approximately 4 volumes via atmospheric distillation. To the resulting solution at room temperature was added BH$_3$.THF (1.0 M THF solution; 67.5 kg) while venting off hydrogen through a flame arrestor. Following completion of the addition, the reaction mixture was heated to 55° C. and stirred for 40 hours. The reaction mixture was quenched by inverse addition to cooled (5° C.) 10% aqueous H$_2$SO$_4$ (13 kg) in a quench vessel, keeping the vessel temperature below 20° C. The contents of the quench vessel were then warmed to 25° C. and stirred for 12 hours, then cooled to 5° C. and the pH of the reaction mixture was adjusted to 9-10 by addition of aqueous ammonium hydroxide (23.4 kg). The reaction mixture was then warmed to 40° C., and the layers are separated. The organic phase was concentrated to about 4 volumes by atmospheric distillation and isopropyl acetate (94.8 kg) was added. The organic phase was washed with dilute brine (20.9 kg) and acidified by addition of 6N HCl in IPA (5.25 kg). Distillation of the remaining THF and IPA caused precipitation of the product. After cooling to 0° C., the product was isolated by filtration, washed with isopropyl acetate and dried under vacuum at 60° C. to afford C—[(R)-6-(3-Fluoro-phenylsulfanyl)-1,2,3,4-tetrahydro-naphthalen-1-yl]-methylamine hydrochloride (4.64-kg): MP=195.7-196.2° C.; H$^1$ NMR (300 MHz): δ ppm (DMSO): 1.59-1.99 (3H, m), 2.6-2.80 (2H, m), 2.92 (1H, dd, J=12.81, 12.43), 3.06 (1H, dd, J=3.77, 12.81 Hz), 3.24 (1H, m), 6.99-7.12 (3H, m), 7.19-7.25 (2H, m), 7.33-7.43 (2H, m), 8.45 (2H, bs, NH); [α]$_D$=−0.3° (MeOH). Chiral Assay (Area Norm): Column: Chiralpak IA (150×4.6 mm), mobile phase 80/20 hexane/ethanol(isocratic), flow rate 1.0 ml/min, 25° C., uv @230 nm.: (R)-isomer 99.17/(S)-isomer 0.83.

Step 8 [(R)-6-(3-Fluoro-phenylsulfanyl)-1,2,3,4-tetrahydro-naphthalen-1-ylmethyl]-urea (R)-6-(3-fluorophenylsulfanyl)-1,2,3,4-tetrahydronaphthalen-1-methylamine hydrochloride salt (4.6 kg) and urea (3.4 kg) were suspended in fresh NMP (9.5 kg). Concentrated aqueous 37% HCl (0.15 kg) was added and the reaction mixture was heated to 100° C. for three hours. On completion of reaction (confirmed by HPLC), the reaction mixture was cooled to 60° C. and water (45 kg) was added. The resulting slurry was stirred vigorously while cooling down to 20° C., and the mixture was allowed to sit for 24 hours. The resulting solid was filtered and washed with water. The wet filter cake was taken into toluene (23.6-kg) and heated to 80° C., then washed with water (twice with 13.5 L) and the reaction mixture was cooled to 40° C. [(R)-6-(3-Fluoro-phenylsulfanyl)-1,2,3,4-tetrahydro-naphthalen-1-ylmethyl]-urea crystallized on addition of n-heptane (7.8 kg). The product was filtered and dried under reduced pressure at 50° C. to afford 3.78-kg of [(R)-6-(3-fluoro-phenylsulfanyl)-1,2,3,4-tetrahydro-naphthalen-1-ylmethyl]-urea: MP=115.1-116.0° C.; MS (M+1)=288; H$^1$ NMR (300 MHz): δ ppm (DMSO): 1.59-1.84 (3H, m), 2.59-2.78 (2H, m), 2.86 (1H, m), 3.10 (1H, ddd, J=6.03, 9.04 Hz), 3.28 (1H, ddd, J=5.65, 6.03), 3.34 (1H, s), 5.46 (2H, s, NH), 6.11 (1H, t, J=6.03 Hz) 6.96-7.09 (3H, m), 7.17-7.23 (2H, m), 7.26-7.31 (1H, m), 7.32-7.41 (1H, m): [α]$_D$=25.5° (MeOH). Chiral Assay (Area Norm): Column: Chiralpak AS-H (150×4.6 mm), mobile phase 80/20 hexane/ethanol(isocratic), flow rate 0.7 ml/min, 25° C., uv @230 nm.: (R)-isomer 99.03/(S)-isomer 0.97.

Step 9 [(R)-6-(3-Fluoro-phenylsulfonyl)-1,2,3,4-tetrahydro-naphthalen-1-ylmethyl]-urea A suspension of [(R)-6-(3-fluorophenylsulfanyl)-1,2,3,4-tetrahydronaphthalen-1-ly-methyl]urea (3.76 kg) in methylene chloride (71 kg) was treated with 98% formic acid (1.31 kg.) and 30% aqueous hydrogen peroxide (6.63 kg). The biphasic reaction mixture was stirred at 35° C. for 48 hours, and then water (12 L) was added. The phases were separated, leaving the aqueous peroxide layer in the original reactor for treatment with sodium hydroxide-bisulfite. The organic layer was washed with saturated aqueous sodium bicarbonate (30 kg), water (30 L) and saturated aqueous sodium chloride (38 kg). The organic layer was checked for peroxide content, and then the methylene chloride layer was distilled off and replaced with methanol. The methanol was reduced to about 9 liters under reduced pressure, and the resulting solution was filtered hot to a clean reactor and cooled to 25° C. Water (4 L) was slowly added to the cloud point and the mixture was stirred for three hours until crystallization occurred, and then an additional 6 L of water was added. The product was filtered and washed with chilled filtered methanol-sterile water for irrigation (50:50). The damp cake was dried at 40° C. in a vacuum oven with a nitrogen purge to constant weight to afford 3.95 kg of [(R)-6-(3-fluoro-phenylsulfonyl)-1,2,3,4-tetrahydro-naphthalen-1-ylmethyl]-urea: MP=154.9-156.1° C.; MS (M+1)=362; H$^1$ NMR (300 MHz): δ ppm (DMSO): 1.6-1.82 (3H, m), 2.67-2.83 (1H, m), 2.83-2.96 (1H, m), 3.04-3.14 (1H, ddd, J=5.65, 6.03, 8.67 Hz), 3.21-3.3 (1H, ddd, J=4.90, 6.03, 8.67 Hz), 3.34 (1H, s), 5.46 (2H, s, NH), 6.10 (1H, t, J=5.65 Hz), 7.43-7.47 (1H, m), 7.52-7.59 (1H, ddt, J=1.13, 2.64, 8.67 Hz), 7.64-7.76 (3H, m), 7.79-7.85 (2H, m); [α]$_D$=25.9° (MeOH). Chiral Assay (Area Norm): (Column: Chiralpak IA (150×4.6 mm), mobile phase Ethanol (isocratic), Flow rate 1.0 ml/min, 25° C., uv @230 nm.: (R)-isomer 99.33/(S)-isomer 0.67.

Example 2

N-((R)-6-Benzenesulfonyl-8-fluoro-1,2,3,4-tetrahydro-naphthalen-1-ylmethyl)-acetamide The synthetic procedure used in this Example is outlined in Scheme D.

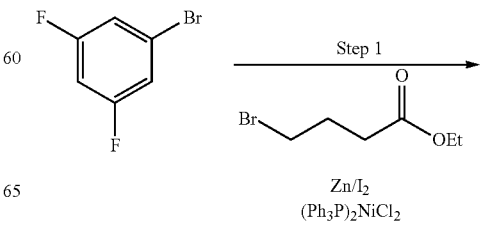

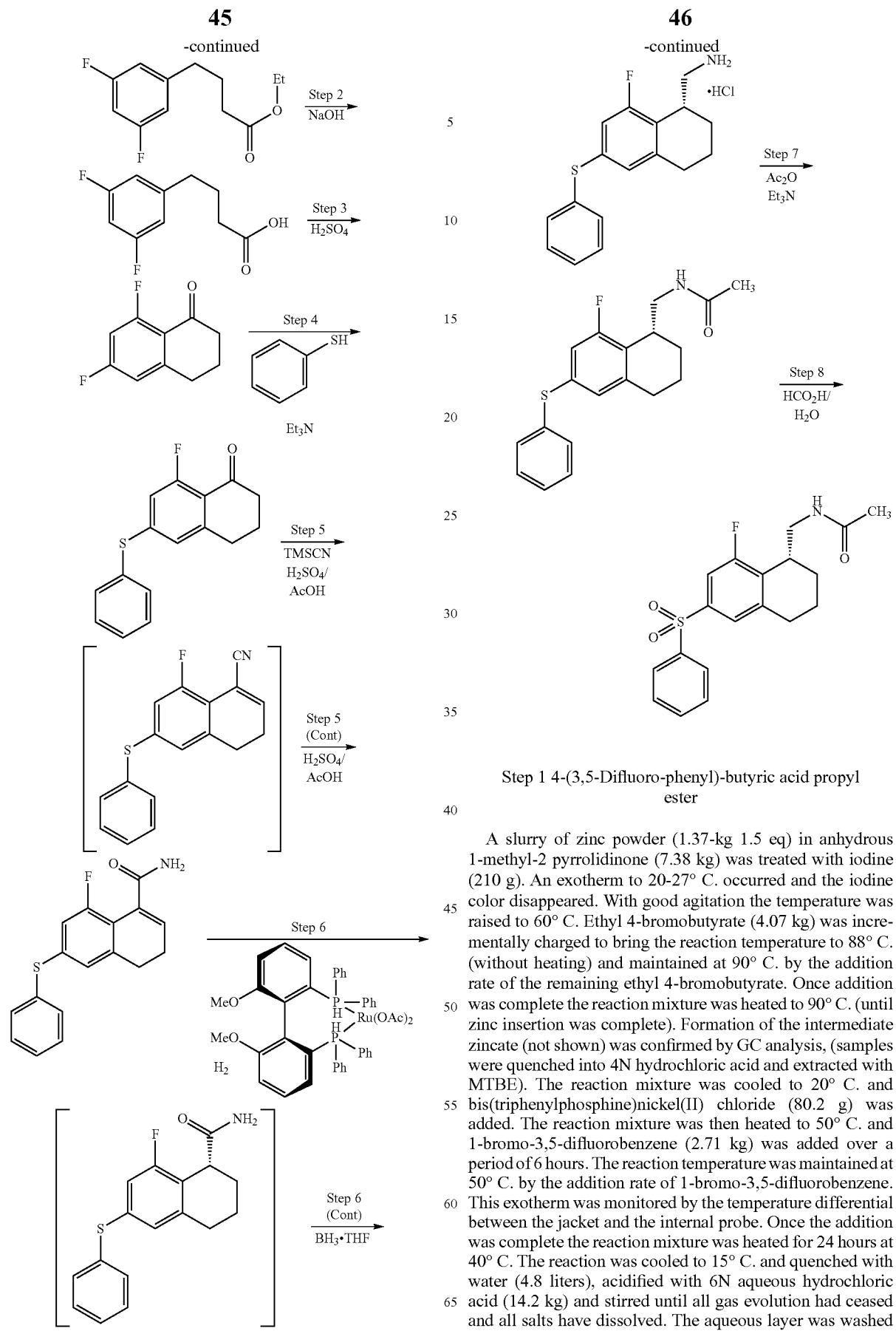

Step 1 4-(3,5-Difluoro-phenyl)-butyric acid propyl ester

A slurry of zinc powder (1.37-kg 1.5 eq) in anhydrous 1-methyl-2 pyrrolidinone (7.38 kg) was treated with iodine (210 g). An exotherm to 20-27° C. occurred and the iodine color disappeared. With good agitation the temperature was raised to 60° C. Ethyl 4-bromobutyrate (4.07 kg) was incrementally charged to bring the reaction temperature to 88° C. (without heating) and maintained at 90° C. by the addition rate of the remaining ethyl 4-bromobutyrate. Once addition was complete the reaction mixture was heated to 90° C. (until zinc insertion was complete). Formation of the intermediate zincate (not shown) was confirmed by GC analysis, (samples were quenched into 4N hydrochloric acid and extracted with MTBE). The reaction mixture was cooled to 20° C. and bis(triphenylphosphine)nickel(II) chloride (80.2 g) was added. The reaction mixture was then heated to 50° C. and 1-bromo-3,5-difluorobenzene (2.71 kg) was added over a period of 6 hours. The reaction temperature was maintained at 50° C. by the addition rate of 1-bromo-3,5-difluorobenzene. This exotherm was monitored by the temperature differential between the jacket and the internal probe. Once the addition was complete the reaction mixture was heated for 24 hours at 40° C. The reaction was cooled to 15° C. and quenched with water (4.8 liters), acidified with 6N aqueous hydrochloric acid (14.2 kg) and stirred until all gas evolution had ceased and all salts have dissolved. The aqueous layer was washed with MTBE (8.04 kg) and the phases were separated. The organic layer was washed with water (9.75 kg). The organic layer was separated and concentrated in vacuo to give 3.3 kg of 4-(3,5-difluoro-phenyl)-butyric acid propyl ester as an oil with a purity of 76.2% by AN HPLC: MS (M+1)=228; $H^1$ NMR (300 MHz): δ(CDCl$_3$): 1.26 (3H, t, J=7.16 Hz), 1.94 (2H, p, J=7.54 Hz), 2.32 (2H, t, J=7.54 Hz), 2.64 (2H, t, J=7.54 Hz), 4.14 (2H, q, J=7.16 Hz), 6.62 (1H, tt, J=2.26, 9.04 Hz), 6.70 (2H, m, J=1.88, 2.26, 6.4 Hz).

Step 2 4-(3,5-Difluoro-phenyl)-butyric acid

A mixture of crude 4-(3,5-difluoro-phenyl)-butyric acid propyl ester (3.3 kg), water (4.4 kg), and 50% sodium hydroxide (3.35 kg) were stirred at 50° C. for 1 hour. The hydrolysis was monitored by HPLC. The resulting solution was washed with hexane (4.2 kg) to remove organic impurities. The aqueous layer was acidified with conc. HCl (4.73 kg), and extracted with MTBE (4.23 kg). The solution was concentrated, and residual MTBE was removed by solvent exchange with n-heptane (4.0 liters) to give crude 4-(3,5-difluoro-phenyl)-butyric acid (2.8 kg) as an oil: $H^1$ NMR (300 MHz): δ(CDCl$_3$): 1.94 (2H, p, J=7.54 Hz), 2.38 (2H, t, J=7.54 Hz), 2.65 (2H, t, J=7.54 Hz), 6.63 (1H, tt, J=2.26, 9.04 Hz), 6.7 (2H, m, J=2.26, 6.4 Hz), 11.70 (1H, bs, COOH)

Step 3
6,8-Difluoro-3,4-dihydro-2H-naphthalen-1-one

A mixture of concentrate sulfuric acid (10.21 kg) and crude 4-(3,5-difluoro-phenyl)-butyric acid (2.8 kg) was stirred at 45° C. until the cyclization reaction was complete by HPLC. The reaction mixture was diluted with water (6.15 kg), and the product was extracted with THF/methylene chloride (2.71/7.33 kg) mixture. The organic layer was sequentially washed with water (4 liters), saturated aqueous sodium bicarbonate (2.64 kg), water (3.0 kg) and 50% diluted brine (8.4 kg). Removal of the solvents provided 1.64 kg (62% yield) of 6,8-difluoro-3,4-dihydro-2H-naphthalen-1-one as a light yellow solid (92.75% pure by HPLC): MP=58.1-58.8° C.; MS (M+1)=183; $H^1$ NMR (300 MHz): δ(DMSO): 2.00 (2H, p, J=6.4 Hz), 2.57 (2H, t, J=6.40 Hz), 2.96 (2H, t, J=6.40 Hz), 7.08-7.20 (2H, m, J=2.26 Hz).

Step 4 8-Fluoro-6-phenylsulfanyl-3,4-dihydro-2H-naphthalen-1-one

A solution of 6,8-difluoro-3,4-dihydro-2H-naphthalen-1-one (1.58 kg) in N,N-dimethylacetamide (4.65 liters) was treated with triethylamine (877 g) and thiophenol (954.9 g) at 20° C. and the reaction mixture was stirred for 19 hours. The reaction mixture was treated with heptane (2.38 liters.), followed by water (9.5 liters) and the precipitate was isolated by filtration and the resulting slurry washed with twice with heptane (790 ml each time), three times with water (1.0 liters each time) and five times with cyclohexane (1.0 liters, each time). The slurry was dried to give 8-fluoro-6-phenylsulfanyl-3,4-dihydro-2H-naphthalen-1-one (1.86 kg, 79% yield) with a purity of 96.2% by HPLC, together with 3.6% yield of the isomer 6-fluoro-8-phenylsulfanyl-3,4-dihydro-2H-naphthalen-1-one: MP=111.7-112.7° C.; MS (M+1)=273; $H^1$ NMR (300 MHz): δ(DMSO): 1.96 (2H, p, J=6.4 Hz), 2.53 (2H, t, J=6.03 Hz), 2.84 (2H, t, J=6.03 Hz), 6.69 (1H, dd, J=1.51, 12.06 Hz), 6.91 (1H, d, J=1.13 Hz), 7.5-7.61 (5H, m, Phenyl).

Step 5 8-Fluoro-6-phenylsulfanyl-3,4-dihydro-naphthalen-1-carboxylic acid amide

8-Fluoro-6-phenylsulfanyl-3,4-dihydro-2H-naphthalen-1-one (1.855 kg, 6.793 moles) from step 4 was dissolved in toluene (3.2 kg) and resulting mixture was distilled under vacuum at 50-55° C. until approximately 2 kg of toluene was removed. The remaining solution was cooled to 20° C. and AlCl$_3$ (37 g) was added. TMSCN (96%, 0.7 kg, 1.0 equiv.) was added over one hour at such a rate that the reaction temperature was kept between 20-50° C. The reaction was monitored for completion by TLC (hexanes/EtOAc 4:1) confirming formation of 8-fluoro-6-phenylsulfanyl-3,4-dihydro-naphthalene-1-carbonitrile, which was not isolated.

The reaction mixture was then cooled to 5° C. and sulfuric acid (1.7 kg) was added slowly, maintaining the internal temperature below 30° C. After 10 minutes the reaction was diluted with acetic acid (9.25 kg, 5.0 vol.), sulfuric acid (6.8 kg, 2.0 vol.) and water (0.93 kg, 0.5 vol). The reaction mixture was then heated to 105° C. while monitoring the reaction progression by HPLC. Once complete (2.0 hours) the reaction was cooled and water (10 vol.) was added. The product was filtered and washed twice with water (5.5 kg each time) and then triturated in a reactor with EtOAc (17 kg) under reflux for 1 hour. The resulting slurry was cooled, filtered and rinsed with twice EtOAc (1.7 kg each time). The product was dried at 35° C. under vacuum to give 1.56 kg of 8-fluoro-6-phenylsulfanyl-3,4-dihydro-naphthalene-1-carboxylic acid amide (77%, 98.3% pure by HPLC): MP=223.6-225.9° C.; MS (M+1)=300; $H^1$ NMR (300 MHz): δ(DMSO): 2.22 (2H, dt, J=7.54 Hz), 2.64 (2H, t, J=7.54 Hz), 6.47 (1H, t, J=4.90 Hz), 6.83 (1H, dd, J=1.88, 10.93 Hz), 7.0 (1H, m), 7.08 (1H, bs, NH), 7.35-7.45 (5H, m, Phenyl), 7.55 (1H, bs, NH).

Step 6 ((R)-8-Fluoro-6-phenylsulfanyl-1,2,3,4-tetrahydro-naphthalen-1-yl)-methylamine hydrochloride A suspension of 8-fluoro-6-phenylsulfanyl-3,4-dihydro-naphthalene-1-carboxylic acid amide (1.46 kg) in methanol (23.2 kg) and [Ru(OAc)$_2$((S)-MeOBIPHEP)] (1.83 g) in methanol (1.5 liters) were combined and subjected to hydrogenation at 40° C. and 150 psig (10.3 bar). Completion of the reaction to form (R)-8-fluoro-6-phenylsulfanyl-1,2,3,4-tetrahydro-naphthalene-1-carboxylic acid amide (not isolated) was monitored by HPLC. The resulting reaction solution was distilled and the solvent exchanged from methanol to THF (7.6 kg). Analysis of an aliquot of the THF solution provided the following data: MP=167.4-168.2° C.; MS (M+1)=302; $H^1$ NMR (300 MHz): δ(DMSO): 1.56-1.84 (2H, m), 1.91 (2H, m), 2.66 (2H, m), 3.67 (1H, t, J=5.65 Hz), 6.80 (1H, dd, J=1.88, 10.17 Hz), 6.88 (1H, bs, NH), 6.92 (1H, m), 7.32-7.44 (6H, m, Phenyl, NH): $[α]_D$=30.5° (MeOH). Chiral Assay (Area Norm): Column: ChiralCel OD-H (250×4.6 mm), mobile phase 85/15 hexane/ethanol(isocratic) Flow rate 0.7 ml/min, 25° C., uv @230 nm.: (R)-isomer 99.32/(S)-isomer 0.68.

The THF solution was treated with Borane THF complex (1.0M THF solution, 22.3 kg) and the resulting reaction mixture was heated to 55° C. at 5 psig for 20 hours. The reaction mixture was then slowly charged into a 10% aqueous sulfuric acid solution (24.3 kg) while keeping the temperature between 5 and 10° C. The resulting solution was treated with 28% aqueous ammonium hydroxide solution (7.05 kg) to adjust the pH to about 10, and was then heated to 40° C. The biphasic system was separated and the organic layer was atmospherically distilled to remove THF solvent, which was then replaced with isopropyl acetate (12.8 kg). The solution was sequentially washed with water (4.0 kg) and brine (5.1 kg). The solution was then cooled to 5° C. and treated with 6N HCl in isopropanol (1.69 kg). The mixture was heated and atmospherically distilled and the solvent was distilled to 90°

C. and replaced with isopropyl acetate. The resulting solid was isolated by filtration, washed with chilled isopropyl acetate (3.84 kg), and dried under vacuum to afford C-((R)-8-fluoro-6-phenylsulfanyl-1,2,3,4-tetrahydro-naphthalen-1-yl)-methylamine hydrochloride (1.38 kg), 87.8% yield, purity 99.5% by HPLC, Chiral HPLC 96.88% ee: MP=232.5-233.8° C.; MS (M+1)=288; H$^1$ NMR (300 MHz): δ(DMSO): 1.55-1.78 (3H, m), 2.08 (1H, bd), 2.55-2.80 (2H, m), 2.89 (2H, bs), 3.31 (1H, bt), 6.85 (1H, dd J=1.51, 10.55 Hz), 6.91 (1H, s), 7.33-7.46 (5H, m), 8.37 (2H, bs, NH$_2$); [α]$_D$=31.8° (MeOH). Chiral Assay (Area Norm): Column: Chiralpak AD-H (150×4.6 mm), mobile phase 95/5 hexane/ethanol with 0.1% isopropylamine(isocratic) Flow rate 0.7 ml/min, 25° C., uv @230 nm.: (R)-isomer 98.44/(S)-isomer 1.56.

Step 7 N-((R)-8-Fluoro-6-phenylsulfanyl-1,2,3,4-tetrahydro-naphthalen-1-ylmethyl)-acetamide A mixture of C-((R)-8-fluoro-6-phenylsulfanyl-1,2,3,4-tetrahydro-naphthalen-1-yl)-methylamine hydrochloride (1.36 kg), DMAP (10 g), acetonitrile (8.6
L), triethylamine (1.27 L), and acetic anhydride (0.41 L) was stirred at 25° C. After thirty minutes water (17.5 L) was added. The resulting slurry was stirred for 30 minutes at 25° C. The product was isolated by filtration and washed with 7.5 L of water. Drying overnight at 50° C. provided 1.34 kg of N4R)-8-fluoro-6-phenylsulfanyl-1,2,3,4-tetrahydro-naphthalen-1-ylmethyl)-acetamide (97.4% yield, 99.66% pure by HPLC, 98.08% ee): MP=94.6-95.9° C.; MS (M+1)=330; H$^1$ NMR (300 MHz): δ(DMSO): 1.44-1.91 (4H, m), 1.83 (3H, s), 2.54-2.79 (2H, m), 3.06 (1H, m), 3.16 (2H, m), 6.83 (1H, dd, =1.51, 10.17 Hz), 6.90 (1H, bs), 7.30-7.45 (5H, m, phenyl), 8.01 (1H, bt, J=5.65 Hz, NH); [α]$_D$=7.4° (MeOH). Chiral Assay (Area Norm): Column: Chiralpak AD-H (150× 4.6 mm), mobile phase 88/12 hexane/ethanol(isocratic) Flow rate 0.7 ml/min, 25° C., uv @230 nm.: (R)-isomer 99.04/(S)-isomer 0.96

Step 8 N-((R)-8-Fluoro-6-phenylsulfonyl-1,2,3,4-tetrahydro-naphthalen-1-ylmethyl)-acetamide N-((R)-8-Fluoro-6-phenylsulfanyl-1,2,3,4-tetrahydro-naphthalen-1-ylmethyl)-acetamide (1.32 kg) was suspended in methylene chloride (8 liters) and treated with 98% formic acid (455 g). The resulting solution is treated with 30% hydrogen peroxide (2.38 kg) in two portions. The temperature was monitored after the addition of the first portion of peroxide and when the temperature stabilized the second portion was added. The reaction mixture was stirred for 23 hours. A fresh charge of formic acid (230-g) and hydrogen peroxide (1.32 kg) was added and the reaction mixture was stirred an additional 12 hours. When the reaction was complete by HPLC, water (1.8 liters) was added and the phases were separated. The methylene chloride layer was washed with saturated sodium bicarbonate solution (5 kg), water (three times 5 liters each time) until the aqueous layer tested negative for peroxide content. The methylene chloride layer was washed with brine (6.54 kg) and concetrated under reduced pressure. The solvent was replaced with methanol. The weight of the residual methanol was adjusted to match the starting input (1.3-kg). The resulting solution was filtered and the solution was treated to cloud point with sterile water to allow crystallization to occur over four hours. More sterile water for irrigation was added until 3.38 kg total had been added and the mixture was stirred until it returned to room temperature. The product was filtered and washed with methanol/sterile water (1:2) and dried under vacuum oven at 50° C. to constant weight to afford N-((R)-8-fluoro-6-phenylsulfonyl-1,2,3,4-tetrahydro-naphthalen-1-ylmethyl)-acetamide (1.4 kg), 99.8% pure by HPLC, Chiral Assay: 98.54% ee R-isomer: MP=152.5-153.8° C.; MS (M+1)=362; H$^1$ NMR (300 MHz): δ(DMSO): 1.45-1.93 (4H, m), 1.84 (3H, s), 2.74 (1H, dq, J=6.03, 10.55 Hz), 2.91 (1H, bdt), 3.17 (3H, m), 7.54-7.75 (5H, m, phenyl), 8.01 (1H, dd, J=1.88, 7.53 Hz), 8.06 (1H, bt, NH); [α]$_D$=39.7° (MeOH). Chiral Assay (Area Norm): Column: Chiralpak IA (150×4.6 mm), mobile phase 20/40/40 hexane/ethanol/methanol(isocratic) Flow rate 0.7 ml/min, 25° C., uv @230 nm.: (R)-isomer 99.27/(S)-isomer 0.73.

Example 3

[(R)-8-Fluoro-6-(3-fluoro-benzenesulfonyl)-1,2,3,4-tetrahydro-naphthalen-1-ylmethyl]-urea The synthetic procedure used in this Example is outlined in Scheme E.

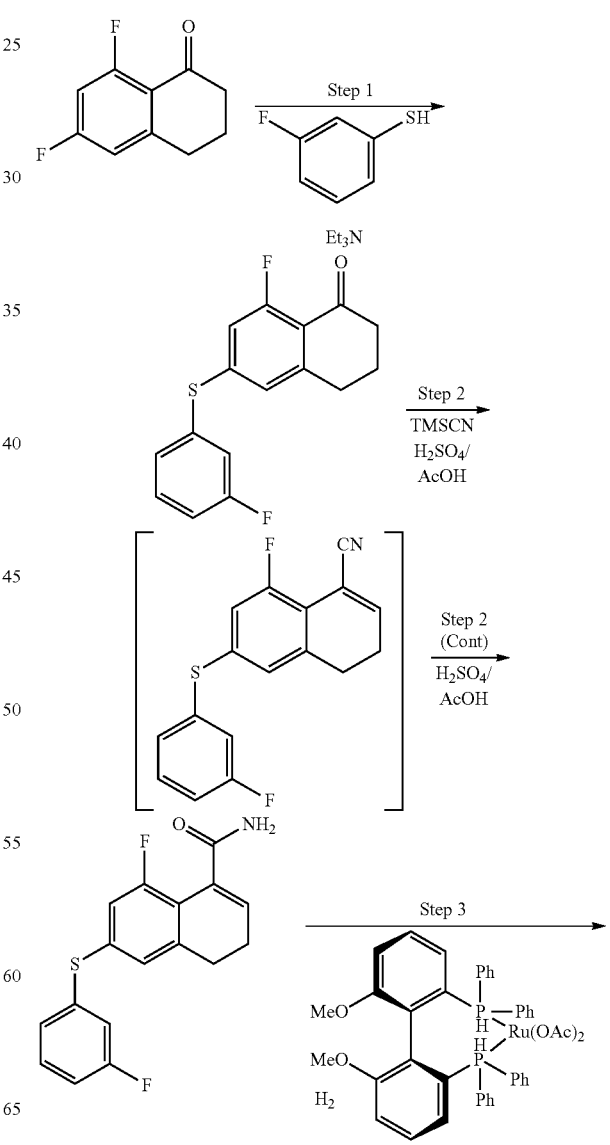

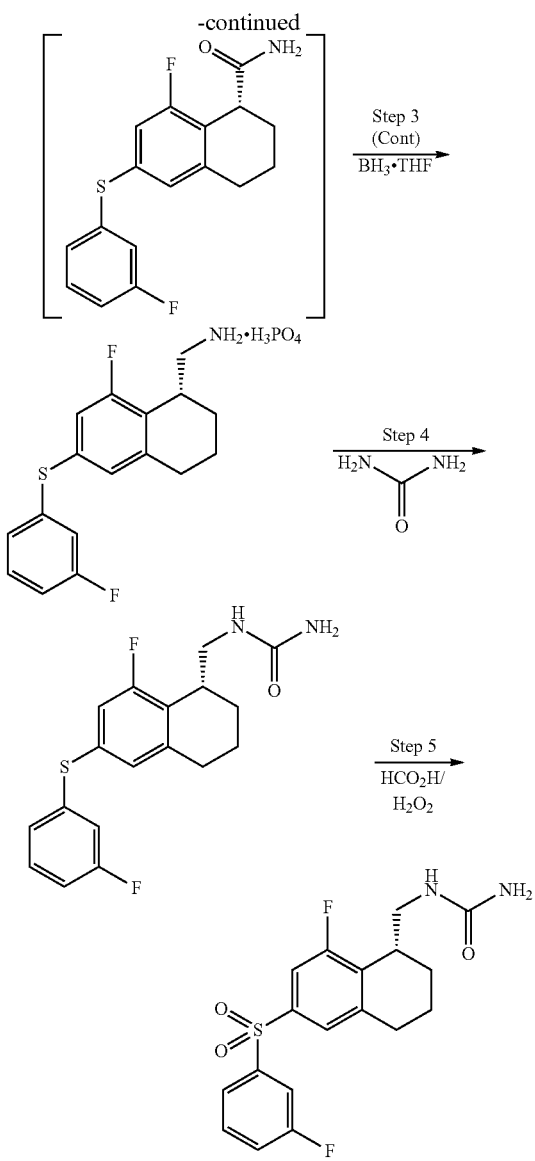

Step 1 8-Fluoro-6-(3-fluoro-phenylsulfanyl)-3,4-dihydro-2H-naphthalen-1-one

A solution of 6,8-difluoro-3,4-dihydro-2H-naphthalen-1-one (50 g) in N,N'dimethylacetamide (100 ml) was treated with triethylamine (38.2 ml), followed by 3-fluorothiophenol (28.2 ml), keeping the temperature below 20° C. The reaction mixture was allowed to stir at ambient temperature for 18 hours. The reaction was diluted with MTBE (70 ml) and cooled on an ice-bath. Water (300 ml) was slowly added (keeping temperature below 25° C.) and the mixture aged for 1 hour. The product was collected by filtration and washed with water and cyclohexane, and dried to afford 8-fluoro-6-(3-fluoro-phenylsulfanyl)-3,4-dihydro-2H-naphthalen-1-one as a pale yellow solid yield (53.5 g, 95% pure by HPLC): MP=126.0-126.9° C.; MS (M+1)=291; H$^1$ NMR (300 MHz): δ (DMSO): 1.97 (2H, pen, J=6.03 Hz), 2.55 (2H, t, J=6.03 Hz), 2.88 (2H, t, J=6.03), 6.84 (1H, dd, J=1.88, 12.06 Hz) 7.01 (1H, d, J=1.03 Hz), 7.31-7.44 (3H, m), 7.52-7.59 (1H, dd/d, J=6.03, 6.41 Hz).

Step 2 8-Fluoro-6-(3-fluoro-phenylsulfanyl)-3,4-dihydro-naphthalene-1-carboxylic acid amide 8-Fluoro-6-(3-fluoro-phenylsulfanyl)-3,4-dihydro-2H-naphthalene-1-one (50 g, 0.17 moles) was dissolved in toluene (100 mL) and the resulting mixture was azeotropically distilled under vacuum at 50 to 55° C. until about 50 ml of toluene was removed. The resulting suspension was cooled to 25° C. and AlCl$_3$ (1 g, 2.0% w/w) was added. TMSCN (96%, 24 mL, 0.17 moles) was then added at a rate such that the reaction temperature was kept between 20 and 50° C. The reaction was monitored for formation of 8-fluoro-6-(3-fluoro-phenylsulfanyl)-3,4-dihydro-naphthalene-1-carbonitrile (which was not isolated) by TLC (Hexanes/EtOAc 4:1). Once complete the reaction was cooled to 5° C. and sulfuric acid (25 mL) was added slowly, maintaining the internal temperature below 30° C. The reaction mixture was stirred and monitored by TLC (Hexanes/EtOAc 4:1). Once complete the reaction was diluted with acetic acid (250 mL), sulfuric acid (100 mL) and water (25 mL). The reaction mixture was heated to 105° C. to distll off volatiles. The reaction temperature was maintained at 100 to 105° C. while monitoring the reaction by HPLC. Once complete the reaction was cooled to 40° C. and quenched with water (500 mL) over one hour at 40 to 45° C. The reaction mixture was cooled to 20° C., filtered in a glass filter funnel and washed thoroughly with water, triturated from EtOAc (500 mL) under reflux for one hour, then slowly cooled to 20° C., filtered in a glass filter funnel, and rinsed with EtOAc. The product was transferred to a drying vacuum oven, and dried at 45° C. under vacuum with nitrogen purge until a constant weight to afford 8-fluoro-6-(3-fluoro-phenylsulfanyl)-3,4-dihydro-naphthalene-1-carboxylic acid amide as a yellow solid (43.1 g), 79% yield, 99% pure by HPLC: MP=212.9-213.7° C.; MS (M+1)=318; H$^1$ NMR (300 MHz): δ (DMSO): 2.25 (2H, m, J=7.91/7.16 Hz), 2.68 (2H, t, J=7.16/7.91 Hz), 6.52 (1H, t, J=4.7 Hz), 7.01 (1H, dd, J=1.51, 10.55 Hz), 7.11 (1H, bs, NH) 7.14-7.23 (4H, m), 7.4-7.49 (1H, m), 7.57 (1H, bs, NH).

Step 3 [(R)-8-Fluoro-6-(3-fluoro-phenylsulfanyl)-1,2,3,4-tetrahydro-naphthalen-1-yl]-methylamine phosphoric acid salt To a degassed solution of 8-fluoro-6-(3-fluorophenysulfanyl)-3.4-dihydronaphthalene-1-carboxamide (42-g) in tetrahydrofuran (420-ml) was added a degassed solution of [Ru(OAc)$_2$((S)-MeOBIPHEP)] (120 mg) in tetrahydrofuran (50 ml). The reaction mixture was subjected to hydrogen gas at 40° C. and 150 psi (10.3 bar) for 20 hours. The reaction was monitored by HPLC for completion of the hydrogenation of the olefin. Solvent was removed under reduced pressure from the intermediate solution of (R)-8-fluoro-6-(3-fluorophenysulfanyl)-1,2,3,4-tetrahydronaphthalene-1-carboxylic acid amide (not isolated), and the remaining liquid was treated with BH$_3$-THF (1 molar solution in THF, 660 ml). The reactor was sealed and heated to 60° C. and stirred for 36 hours. The reaction mixture was quenched into 10% aqueous sulfuric acid (650 ml) at 5° C. The pH of the solution was adjusted with 28% aqueous ammonium hydroxide to 9.4 and the biphasic layers were separated. The organic layer was reduced in volume to about 600 ml, treated with phosphoric acid (18.3 g) and isopropanol (60 ml). The remaining tetrahydrofuran was atmospherically distilled and replaced with isopropanol. The solution was cooled to 5° C. and the resulting slurry was aged and filtered. The product was dried at 60° C. under vacuum with a nitrogen purge to afford 50 g of [(R)-8-fluoro-6-(3-fluoro-phenylsulfanyl)-1,2,3,4-tetrahydro-naphthalen-1-yl]-methylamine phosphoric acid salt (94% yield, 100% pure by HPLC): MP=197.5-199.2° C.; MS (M+1)=306; H$^1$ NMR (300 MHz): δ (DMSO): 1.58-1.85 (3H, m), 2.05-2.16 (1H, m), 2.58-2.78 (2H, m), 2.8 (1H, dd, J=12.43 Hz) 2.94 (1H, dd, J=3.77, 12.81 Hz), 3.21-3.31 (1H, m), 6.90 (1H, dd, J=1.51, 10.17 Hz), 6.97 (1H, s), 7.06-7.17 (3H, m), 7.36-7.44 (1H, m), 7.92 (5H, bs, NH/H$_3$PO$_4$); [α]$_D$=20.9° (MeOH).

Step 4 [(R)-8-Fluoro-6-(3-fluoro-phenylsulfanyl)-1,2,3,4-tetrahydro-naphthalen-1-ylmethyl]-urea (R)-8-Fluoro-6-(3-fluorophenylsulfanyl)-1,2,3,4-tetrahydronaphthalen-1-yl-methylamine phosphate salt was treated with urea (27.5 g) in anhydrous N-methylpyrrolidinone (140 ml) at 100° C. for 18 hours. The reaction was cooled to 70° C. and water (360 ml) was added dropwise while allowing the temperature to decline to room temperature. The resulting solids were collected and washed with water. The crude filter cake (46 g) was recrystallized from toluene (160 ml) and n-heptane (60 ml) to afford [(R)-8-fluoro-6-(3-fluoro-phenylsulfanyl)-1,2,3,4-tetrahydro-naphthalen-1-ylmethyl]-urea (37.27 g) in 93.8% yield, 99.8% pure by HPLC: MP=130.7-132.4° C.; MS (M+1)=349; H$^1$ NMR (300 MHz): δ (DMSO): 1.49-1.99 (4H, m), 2.57-2.83 (2H, dt/m), 3.99-3.27 (3H, m), 5.43 (2H, bs, NH), 6.20 (1H, bt, J=6.03), 6.96-7.04 (2H, m), 7.1-7.17 (3H, m), 7.37-7.47 (1H, m); [α]$_D$=24.2° (MeOH).

Step 5 [(R)-8-Fluoro-6-(3-fluoro-benzenesulfonyl)-1,2,3,4-tetrahydro-naphthalen-1-ylmethyl]-urea (R)-8-Fluoro-6-(3-fluorophenylsulfanyl)-1,2,3,4-tetrahydronaphthalen-1-ylmethylurea (36-g) in dichloromethane was treated with formic acid (11.9 g) and 30% aqueous hydrogen peroxide with stirring for 18 hours. The reaction mixture was diluted with methylene chloride (1 liter) and water (200 ml) to dissolve the resulting solids. The layers were separated and the organic layer was sequentially washed with saturated aqueous sodium bicarbonate (200 ml), water (three times with 200 ml) until the organic layer was free of peroxide. The methylene chloride layer was filtered and distilled to a minimum volume and the resulting solids were collected. The crude product was recrystallized from methanol (720 ml), filtered, and dried in a vacuum oven at 50° C. to afford [(R)-8-fluoro-6-(3-fluoro-benzenesulfonyl)-1,2,3,4-tetrahydro-naphthalen-1-ylmethyl]-urea (37 g) in 95% yield), 99.7% and 99.8% chiral by HPLC: MP=193.5-194.4° C.; MS (M+1)=381; H$^1$ NMR (300 MHz): δ (DMSO): 1.46-1.96 (4H, m), 2.66-2.80 (1H, ddd, J=6.40, 10.55 Hz), 2.84-2.96 (1H, dt) 3.00-3.22 (3H, m) 5.40 (2H, bs, NH$_2$), 6.20 (1H, bt, J=6.40 Hz, NH) 7.57 (1H, dd, J=1.13, 8.29 Hz), 7.62 (1H, s/m), 7.64-7.74 (2H, ddd, J=5.27, 5.65, 8.29 Hz), 7.83-7.93 (2H, ddt, J=1.88, 2.26, 7.54, 8.29 Hz); [α]$_D$=25.7° (MeOH). Chiral Assay (Area Norm): Column: Chiralpak IA (150×4.6 mm), mobile phase ethanol(isocratic) Flow rate 0.7 ml/min, 25° C., uv @247 nm.: (R)-isomer 99.94/(S)-isomer 0.06.

Example 4

Chiral Catalyst Comparison: (R)— and (S)—6-(3-Fluoro-phenylsulfanyl)-1,2,3,4-tetrahydro-naphthalene-1-carboxylic acid amide The synthetic procedure used in this Example is outlined in Scheme F.

SCHEME F

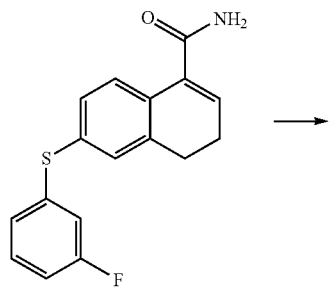

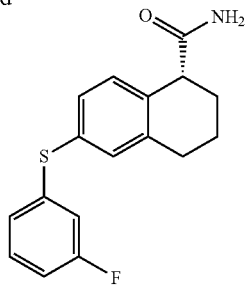

In a glove box (O$_2$ content≤2 ppm) a 6 ml autoclave equipped with a glass insert and a magnetic stirring bar was charged with 50 mg (0.167 mmol) of 6-(3-fluoro-phenylsulfanyl)-3,4-dihydro-naphthalene-1-carboxylic acid amide, 6.45 mg (0.00668 mmol) of [Ru(trifluoroacetate)$_2$((S)-pTol-MeOBIPHEP)] (S/C 25) and 1 ml of methanol. The asymmetric hydrogenation was run for 19.5 hours at 40° C. under 40 bar of hydrogen. After cooling to room temperature the pressure was released from the autoclave, the methanol solution was filtered through a silicagel pad and evaporated in vacuo to give (R)-6-(3-fluoro-phenylsulfanyl)-1,2,3,4-tetrahydro-naphthalene-1-carboxylic acid amide in quantitative yield and with an enantiomeric ratio of 99:1. The conversion was >=99.9%.

The enantiomeric ratio was determined by HPLC using a Chiralcel-AS-H column, 25 cm*4.6 mm. Eluents: 40% n-heptane, 50% ethanol, 10% heptane with 0.1% diethyl amine. Flow: 1 ml/min, 40° C., 1 μl. Injection volume: 210 nm. Retention times: (R)-6-(3-fluoro-phenylsulfanyl)-1,2,3,4-tetrahydro-naphthalene-1-carboxylic acid amide 7.3 min, 6-(3-Fluoro-phenylsulfanyl)-3,4-dihydro-naphthalene-1-carboxylic acid amide 8.3 min, (S)-6-(3-Fluoro-phenylsulfanyl)-1,2,3,4-tetrahydro-naphthalene-1-carboxylic acid amide 9.7 min.

The above procedure was repeated using different chiral ruthenium catalysts to produce corresponding (R) and (S) isomers of 6-(3-Fluoro-phenylsulfanyl)-1,2,3,4-tetrahydro-naphthalene-1-carboxylic acid amide. The results are shown in Table 2, together with catalyst, time, % conversion and enantiomeric ratio. Reaction scale was in all experiments 50 mg, temperature was 40° C. Examples 4.6 to 4.23 have been run at S/C 50.

TABLE 2

| Example | Catalyst | Time (hours) | Conversion (%) | Ratio R:S |
|---|---|---|---|---|
| 4.1 | [Ru(OAc)$_2$((R)-iPr-MeOBIPHEP)] | 19.5 | >99.9 | 3:97 |
| 4.2 | [RuCl((R,R)-Et-Duphos)(p-cymene)]Cl | 19.5 | 20 | 67:33 |
| 4.3 | [Ru(OAc)$_2$((S)-(3,5-iPr,4-MeO)-MeOBIPHEP)] | 19.5 | 99.8 | 99:1 |
| 4.3 | Ru(OAc)$_2$((all-S)-BICP) | 19.5 | 99.7 | 75:25 |
| 4.5 | [Ru(OAc)$_2$((S,R)-PPF-P(tBu)$_2$)]$^{a)}$ | 19.5 | 99.6 | 95:5 |
| 4.6 | [Ru(OAc)$_2$((R)-BIPHEMP)] | 22.5 | 100 | 2:98 |
| 4.7 | [Ru(trifluoroacetate)$_2$((S)-TriMeOPHEP)] | 22.5 | 100 | 99:1 |
| 4.8 | [Ru(OAc)$_2$((R)-(2-Furyl)-MeOBIPHEP)] | 22.5 | 99.8 | 3:97 |
| 4.9 | [Ru(OAc)$_2$((R)-Cy-MeOPHEP)] | 22.5 | 100 | 2:98 |
| 4.10 | [Ru(OAc)$_2$((S)-3,5-tBu-MeOBIPHEP)] | 22.5 | 100 | 99:1 |
| 4.11 | [Ru(OAc)$_2$((S)-3,5-tBu,4-MeO-MeOBIPHEP)] | 22.5 | 100 | 98:2 |

TABLE 2-continued

| Example | Catalyst | Time (hours) | Conversion (%) | Ratio R:S |
|---|---|---|---|---|
| 4.12 | [Ru(OAc)$_2$((S)-3,5-TMS-MeOBIPHEP)] | 22.5 | 100 | >99:1 |
| 4.13 | [Ru(OAc)$_2$((S)-3,5-Me,4-MeO-MeOBIPHEP)] | 22.5 | 100 | 98:2 |
| 4.14 | [Ru(OAc)$_2$((S)-3,5-Ipr,4-MeO-MeOBIPHEP)] | 22.5 | 100 | 99:1 |
| 4.15 | [Ru(OAc)$_2$((R)-(2-Furyl)-BIPHEMP)] | 22.5 | 100 | 8:92 |
| 4.16 | [RuI((S)-MeOBIPHEP)(p-cymene)]I b) | 22.5 | 100 | 99:1 |
| 4.17 | [RuCl((S)-MeOBIPHEP)-(benzene)]Cl b) | 22.5 | 100 | 99:1 |
| 4.18 | [Ru(OAc)$_2$((R)-BITIANP)] | 22.5 | 100 | 3:97 |
| 4.19 | [Ru(OAc)$_2$((R)-BenzoylO-BIPHEP)] | 22.5 | 100 | 2:98 |
| 4.20 | [RuCl$_2$((S)-3,5-Xyl-MeO-BIPHEP)((S,S)-DPEN)] | 22.5 | 100 | 98:2 |
| 4.21 | [RuCl$_2$((S)-3,5-Xyl-MeO-BIPHEP)((R,R)-DPEN)] | 22.5 | 100 | 99:1 |
| 4.22 | [RuCl$_2$((S)-3,5-tBu-MeO-BIPHEP)((rac)-DPEN)] | 22.5 | 100 | 99:1 |
| 4.23 | [Ru((S)-(3,5-tBu-MeOBIPHEP)(DMF)$_4$][BF$_4$]$_2$ b) | 22.5 | 100 | >99:1 |

$^{a)}$Prepared in-situ from [Ru(OAc)$_2$(cyclooctadiene)] and diphosphine.
b) Prepared by addition of 2 molar equivalents of HBF$_4$ to [Ru(OAc)$_2$((S)-(3,5-tBu-MeO-BIPHEP)] in DMF The above procedure was used with several chiral ruthenium catalysts, but replacing the methanol solvent with trifluoroethanol. The trifluoroethanol results are shown in Table 3.

TABLE 3

| Example | Catalyst | Time (hours) | Conversion (%) | Ratio R:S |
|---|---|---|---|---|
| 4.24 | [Ru(trifluoroacetate)$_2$((S)-pTol-MeOBIPHEP] | 20 | >99.9 | 90:10 |
| 4.25 | [Ru(OAc)$_2$((R)-iPr-MeOBIPHEP)] | 20 | >99.9 | 38:62 |
| 4.26 | [RuCl((R,R)-Et-Duphos)(p-cymene)]Cl | 20 | 1.5 | — |
| 4.27 | [Ru(OAc)$_2$((S)-(3,5-iPr,4-MeO)-MeOBIPHEP)] | 20 | 99.9 | 81:19 |
| 4.28 | [Ru(OAc)$_2$((all-S)-BICP)] | 20 | 99.7 | 32:68 |
| 4.29 | [Ru(OAc)$_2$((S,R)-PPF-P(tBu)$_2$)]$^{a)}$ | 20 | 99.7 | 90:10 |

$^{a)}$Prepared in-situ from [Ru(OAc)$_2$(cyclooctadiene)] and diphosphine.

As can be seen from Tables 2 and 3, asymmetric reduction in methanol produced better (more specific) enantioselectivity than the corresponding reaction in trifluoroethanol. [RuCl((R,R)-Et-Duphos)(p-cymene)]Cl was the poorest catalyst in methanol in terms of yield and enantioselectivity, and was essentially non-reactive in trifluoroethanol. [Ru(OAc)$_2$(iPr-MeOBIPHEP)] and [Ru(OAc)$_2$(PPF-P(tBu)$_2$)] provided high enantioselectivity for both (R) and (S) enantiomers.

Example 5

Chiral Catalyst Comparison: (R)— and (S)—6-(3-Fluoro-phenylsulfanyl)-1,2,3,4-tetrahydro-naphthalene-1-carboxylic acid amide under acidic conditions In a glove box (O$_2$ content≤2 ppm) a catalyst solution was prepared in the glass insert of a 6 ml autoclave by reacting a solution of 6.45 mg (0.00668 mmol) of [Ru(trifluoroacetate)$_2$((S)-pTol-MeOBIPHEP)] (S/C 25) in 0.5 ml of methanol with 0.5 ml of methanol containing 0.020 mmol of HCl and stirring for 2 h at room temperature. After addition of 50 mg (0.167 mmol) of 6-(3-Fluoro-phenylsulfanyl)-3,4-dihydro-naphthalene-1-carboxylic acid amide, the asymmetric hydrogenation was run for 18 hours at 40° C. under 40 bar of hydrogen. After cooling to room temperature the pressure was released from the autoclave, the methanol solution was filtered through a silicagel pad and evaporated in vacuo to give (R)-6-(3-Fluoro-phenylsulfanyl)-1,2,3,4-tetrahydro-naphthalene-1-carboxylic acid amide in quantitative yield and with an enantiomeric ratio of 98.8:1.2. The conversion was >=99.9%.

The reaction was repeated with other catalysts according to the procedure above, and the results are shown in Table 4. Reaction scale was in all experiments 50 mg, temperature was 40° C.

TABLE 4

| Example | Catalyst | Time (Hours) | Conversion (%) | Ratio R:S |
|---|---|---|---|---|
| 5.1 | [Ru(OAc)$_2$((R)-iPr-MeOBIPHEP)] + 3HCl | 18 | 13 | 15:85 |
| 5.2 | [Ru(OAc)$_2$((R,R)-Et-Duphos)] + 3 HCl | 18 | 27 | 63:37 |
| 5.3 | [Ru(OAc)$_2$((S)-(3,5-iPr,4-MeO)-MeOBIPHEP)] + 3HCl | 18 | 99.6 | 99:1 |
| 5.4 | [Ru(OAc)$_2$((all-S)-BICP)] + 3HCl | 18 | 99.8 | 82:18 |
| 5.5 | [Ru(OAc)$_2$((S,R)-PPF-P(tBu)2)]$^{a)}$ + 3HCl | 18 | 99.9 | 99:1 |

$^{a)}$prepared in-situ from [Ru(OAc)$_2$(cyclooctadiene)] + diphosphine.

Example 6

(R)-6-(3-Fluoro-phenylsulfanyl)-1,2,3,4-tetrahydro-naphthalene-1-carboxylic acid amide In a glove box (O$_2$ content≤2 ppm) a 35 ml autoclave equipped with a glass insert and a magnetic stirring bar was charged with 250 mg (0.835 mmol) of 6-(3-Fluoro-phenylsulfanyl)-3,4-dihydro-naphthalene-1-carboxylic acid amide, 4.03 mg (0.00418 mmol) of [Ru(trifluoroacetate)$_2$((S)-pTol-MeOBIPHEP)] (S/C 200) and 3 ml of methanol. The asymmetric hydrogenation was run for 24 h at 40° C. under 40 bar of hydrogen. After cooling to room temperature the pressure was released from the autoclave, the methanol solution was evaporated in vacuo. The residue was dissolved in 4 ml of dichloromethane and filtered through a silicagel pad, which was washed with a total of 6 ml of dichloromethane. Evaporation of the filtrate and drying (50° C./10 mbar/2 hours) afforded 232 mg of (R)-6-(3-Fluoro-phenylsulfanyl)-1,2,3,4-tetrahydro-naphthalene-1-carboxylic acid amide as a light yellow solid with an enantiomeric ratio of 99:1. The conversion was >=99.9%.

Example 7

(R)-6-(3-Fluoro-phenylsulfanyl)-1,2,3,4-tetrahydro-naphthalene-1-carboxylic acid amide In a glove box (O$_2$ content≤2 ppm) a 35 ml autoclave equipped with a glass insert and a magnetic stirring bar was charged with 0.40 g (1.336 mmol) of 6-(3-Fluoro-phenylsulfanyl)-3,4-dihydro-naphthalene-1-carboxylic acid amide, 1.29 mg (0.00134 mmol) of [Ru(trifluoroacetate)$_2$((S)-pTol-MeOBIPHEP)] (S/C 1000) and 4 ml of methanol. The asymmetric hydrogenation was run for 24 h at 40° C. under 40 bar of hydrogen. After cooling to room temperature the pressure was released from the autoclave, the methanol solution was evaporated in vacuo. Isolation as described in example 4 afforded after drying 405 mg of (R)-6-(3-Fluoro-phenylsulfanyl)-1,2,3,4-tetrahydro-naphthalene-1-carboxylic acid amide as a light yellow solid with an enantiomeric ratio of 99:1. The conversion was >=99.9%.

The reaction was repeated with other catalysts according to the procedure above, and the results are shown in Table 5. Reaction scale was in all experiments 0.40 g, temperature was 40° C., hydrogen pressure in examples 7.3, 7.5 was 10 bar.

TABLE 5

| Example | Catalyst | Time (Hours) | Conversion (%) | Ratio R:S |
|---|---|---|---|---|
| 7.1 | [Ru(trifluoroacetate)$_2$((S)-pTol-MeOBIPHEP)] | 24 | 99.9 | 99:1 |
| 7.2 | [Ru(OAc)$_2$((S)-pTol-MeOBIPHEP)] | 24 | 99.9 | 99:1 |
| 7.3 | [Ru(OAc)$_2$((S)-pTol-MeOBIPHEP)] | 24 | 99.7 | 99:1 |
| 7.4 | [Ru(OAc)$_2$((S)-MeOBIPHEP)] | 24 | 99.7 | 99:1 |
| 7.5 | [Ru(OAc)$_2$((S)-MeOBIPHEP)] | 24 | 99.7 | 99:1 |

Example 8

(R)-6-(3-Fluoro-phenylsulfanyl)-1,2,3,4-tetrahydro-naphthalene-1-carboxylic acid amide In a glove box (O$_2$ content≤2 ppm) a 50 ml autoclave equipped with a mechanical stirrer was charged with 4.00 g (13.36 mmol) of 6-(3-Fluoro-phenylsulfanyl)-3,4-dihydro-naphthalene-1-carboxylic acid amide, 1.07 mg (0.00134 mmol) of [Ru(OAc)$_2$((S)-MeOBIPHEP)] (S/C 10000) and 28 ml of methanol. The asymmetric hydrogenation was run for 18 h at 40° C. under 9 bar of hydrogen. After cooling to room temperature the pressure was released from the autoclave, the methanol solution was evaporated in vacuo. Isolation as described in example 4 afforded after drying (R)-6-(3-Fluoro-phenylsulfanyl)-1,2,3,4-tetrahydro-naphthalene-1-carboxylic acid amide in quantitative yield as an off-white solid with an enantiomeric ratio of 99:1. The conversion was >=99.8%.

The reaction was repeated with other catalysts according to the procedure above, and the results are shown in Table 6. Reaction scale in experiments 8.1 to 8.4 was 4.00 g, in experiments 8.5 to 8.10 was 2 g.

Example 9

(R)-6-(3-Fluoro-phenylsulfanyl)-1,2,3,4-tetrahydro-naphthalene-1-carboxylic acid amide In a glove box (O$_2$ content≤2 ppm) a 35 ml autoclave equipped with a glass insert and a magnetic stirring bar was charged with 0.40 g (1.336 mmol) of 6-(3-Fluoro-phenylsulfanyl)-3,4-dihydro-naphthalene-1-carboxylic acid amide, 2.36 mg (0.00267 mmol) of [Ru(OAc)$_2$((S)-MeOBIPHEP)] (S/C 500) and 4 ml of ethanol. The asymmetric hydrogenation was run for ca. 16 h at 40° C. under 40 bar of hydrogen. After cooling to room temperature the pressure was released from the autoclave, the ethanol solution was evaporated in vacuo. Isolation as described in example 4 afforded after drying (R)-6-(3-Fluoro-phenylsulfanyl)-1,2,3,4-tetrahydro-naphthalene-1-carboxylic acid amide in virtually quantitative yield as a light yellow solid with an enantiomeric ratio of 99:1. The conversion was >=99.9%.

The reaction was repeated in other solvents according to the procedure above, and the results are shown in Table 7. Reaction scale was in all experiments 0.40 g, temperature was 40° C., hydrogen pressure was 40 bar.

TABLE 7

| Example | Solvent (vol/vol) | Time (hours) | Conversion (%) | Ratio R:S |
|---|---|---|---|---|
| 9.1 | MeOH | 16.5 | 100 | 99:1 |
| 9.2 | i-PrOH | 16.5 | 100 | 98:2 |
| 9.3 | CH$_2$Cl$_2$ | 16.5 | 48 | 97:3 |
| 9.4 | CH2Cl2/MeOH (2/2) | 21 | 100 | 99:1 |
| 9.5 | THF/MeOH (2/2) | 18.5 | 100 | 99:1 |
| 9.6 | THF/toluene (2/2) | 18.5 | 92 | 98:2 |

Example 10

Radioligand Binding Studies

This example illustrates in vitro radioligand binding studies of compound of formula I.

The binding activity of compounds of this invention in vitro was determined as follows. Duplicate determinations of 5-HT$_6$ ligand affinity were made by competing for binding of [$^3$H]LSD in cell membranes derived from HEK293 cells stably expressing recombinant human 5-HT$_6$ receptor. Duplicate determinations of 5-HT$_{2A}$ ligand affinity were made by competing for binding of [$^3$H]Ketanserin (3-(2-(4-(4-fluorobenzoyl)piperidinol)ethyl)-2,4(1H,3H)-quinazolinedione) in cell membranes derived from CHO-K1 cells stably

TABLE 6

| Example | Catalyst | T ° C. | Time (Hours) | Conversion (%) | Ratio R:S |
|---|---|---|---|---|---|
| 8.1 | [Ru(OAc)$_2$((S)-pTol-MeOBIPHEP)] | 40 | 18 | 99.7 | 99:1 |
| 8.2 | [Ru(trifluoroacetate)$_2$((S)-MeOBIPHEP)] | 40 | 18 | 100 | 99:1 |
| 8.3 | [Ru(OAc)$_2$((S)-MeOBIPHEP)] + 5HBF$_4$ | 40 | 18 | 99.1 | 99:1 |
| 8.4 | [RuCl((S)-MeOBIPHEP)(p-cymene)]Cl | 40 | 18 | 100 | 98:2 |
| 8.5 | [Ru(OAc)$_2$((S)-MeOBIPHEP)] | 20 | 19 | 67 | 99:1 |
| 8.6 | [Ru(OAc)$_2$((S)-MeOBIPHEP)] | 60 | 3.5 | 100 | 98:2 |
| 8.7 | [Ru(OAc)$_2$((S)-MeOBIPHEP)] | 80 | 2.5 | 100 | 97:3 |
| 8.8 | [Ru(trifluoroacetate)$_2$((S)-MeOBIPHEP)] | 20 | 22 | 87 | 99:1 |
| 8.9 | [Ru(trifluoroacetate)$_2$((S)-MeOBIPHEP)] | 60 | 3.5 | 100 | 98:2 |
| 8.10 | [Ru(trifluoroacetate)$_2$((S)-MeOBIPHEP)] | 80 | 2 | 100 | 97:3 |
| 8.11 a) | [Ru(OAc)$_2$((S)-MeOBIPHEP)] | 40 | 20 | 100 | 99:1 | a) This experiment was run on a 20 g scale under 40 bar of hydrogen.

expressing recombinant human 5-HT$_{2A}$ receptor. Membranes were prepared from HEK 293 cell lines by the method described by Monsma et al., Molecular Pharmacology, Vol. 43 pp. 320-327 (1993), and from CHO-K$^1$ cell lines as described by Bonhaus et al., Br J. Pharmacol. June; 115(4): 622-8 (1995).

For estimation of affinity at the 5-HT$_6$ receptor, all determinations were made in assay buffer containing 50 mM Tris-HCl, 10 mM MgSO$_4$, 0.5 mM EDTA, 1 mM ascorbic acid, pH 7.4 at 37° C., in a 250 microliter reaction volume. For estimation of affinity at the 5-HT$_{2A}$ receptor all determinations were made in assay buffer containing 50 mM Tris-HCl, 5 mM ascorbic acid, 4 mM CaCl$_2$, pH 7.4 at 32° C., in a 250 microliter reaction volume.

Assay tubes containing [$^3$H] LSD or [$^3$H]Ketanserin (5 nM), competing ligand, and membrane were incubated in a shaking water bath for 75 min. at 37° C. (for 5-HT$_6$) or 60 min. at 32° C. (for 5-HT$_{2A}$), filtered onto Packard GF-B plates (pre-soaked with 0.3% PEI) using a Packard 96 well cell harvester and washed 3 times in ice cold 50 mM Tris-HCl. Bound [$^3$H] LSD or [$^3$H]Ketanserin were determined as radioactive counts per minute using Packard TopCount.

Displacement of [$^3$H]LSD or [$^3$H]Ketanserin from the binding sites was quantified by fitting concentration-binding data to a 4-parameter logistic equation:

$$\text{binding} = \text{basal} + \left( \frac{Bmax - \text{basal}}{1 + 10^{-Hill(log[ligand] - logIC_{50})}} \right)$$

where Hill is the Hill slope, [ligand] is the concentration of competing radioligand and IC$_{50}$ is the concentration of radioligand producing half-maximal specific binding of radioligand. The specific binding window is the difference between the Bmax and the basal parameters.

Using the procedures of this Example, the compounds (R)-[6-(3-Fluoro-benzenesulfonyl)-1,2,3,4-tetrahydro-naphthalen-1-ylmethyl]-urea, [(R)-8-Fluoro-6-(3-fluoro-benzenesulfonyl)-1,2,3,4-tetrahydro-naphthalen-1-ylmethyl]-urea and (R)—N-(6-Benzenesulfonyl-8-fluoro-1,2,3,4-tetrahydro-naphthalen-1-ylmethyl)-acetamide showed a pKi for 5-HT6 of 10.0, 9.8 and 9.75 respecvively.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

The invention claimed is:

1. A method of producing a compound of formula k1 or k2

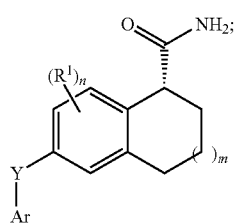

k1

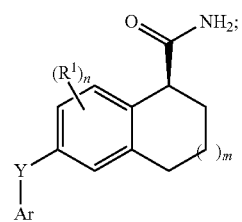

k2 wherein:
m is 1;
n is 0 or 1;
Ar is: 3-fluoro-phenyl; or unsubstituted phenyl;
Y is —SO$_2$—; and
R$^1$ is: fluoro;
the method comprising:
reducing a dihydronapthalene amide compound of formula i

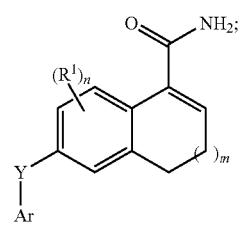

i with hydrogen gas in the presence of a catalyst of formula j1 or j2

Ru(Z)$_2$(L)                            j1;

Ru(E)(E')(L)(D)                        j2;

wherein:
D is an optionally chiral diamine;
E and E' are both halo, or E is hydrogen and E' is BH$_4$;
L is a chiral diphosphine ligand; and
Z is: halo or R$^b$—CO$_2^-$ (carboxylate) wherein R$^b$ is: C$_{1-6}$alkyl; halo-C$_{1-6}$alkyl; C$_{1-6}$alkoxy; aryl optionally substituted with halo; or heteroaryl optionally substituted with halo.

2. The method of claim 1, wherein n is 0.
3. The method of claim 1, wherein n is 1.
4. The method of claim 1, wherein the catalyst is j1.
5. The method of claim 1, wherein the catalyst is j2.
6. The method of claim 1, wherein Ar is 3-fluoro-phenyl.
7. The method of claim 1, wherein Ar is unsubstituted phenyl.
8. The method of claim 1, wherein Z is acetate.
9. The method of claim 1, wherein the chiral diphosphine ligand L is the (R) or (S)-enantiomer of MeOBIPHEP.
10. The method of claim 1, wherein L is (6,6'-dimethoxy-biphenyl-2,2'diyl)bis(diphenylphosphine).
11. The method of claim 1, wherein the catalyst is [Ru(OAc)$_2$((S)MeOBIPHEP)] or [Ru(OAc)$_2$((R)-MeOBIPHEP)].

12. The method of claim 1, further comprising:
reducing a compound of formula k1 or k2 k1

[Structure: tetrahydronaphthalene with C(O)NH₂ group, (R¹)ₙ, Y-Ar, and (   )ₘ]

k2

[Structure: tetrahydronaphthalene with C(O)NH₂ group, (R¹)ₙ, Y-Ar, and (   )ₘ]

to provide a compound of formula m1 or m2 m1

[Structure: tetrahydronaphthalene with CH₂NH₂ group, (R¹)ₙ, Y-Ar, and (   )ₘ]

m2

[Structure: tetrahydronaphthalene with CH₂NH₂ group, (R¹)ₙ, Y-Ar, and (   )ₘ]

wherein m, n, Y, Ar and R¹ are as recited in claim 1.

13. The method of claim 12, further comprising:
reacting a compound of formula m1 or m2 m1

[Structure: tetrahydronaphthalene with CH₂NH₂ group, (R¹)ₙ, Y-Ar, and (   )ₘ]

m2

[Structure: tetrahydronaphthalene with CH₂NH₂ group, (R¹)ₙ, Y-Ar, and (   )ₘ]

with a reagent of formula n

X-R²      n;

to form a compound of formula of o1 or o2 o1

[Structure: tetrahydronaphthalene with CH₂NHR² group, (R¹)ₙ, Y-Ar, and (   )ₘ]

o2

[Structure: tetrahydronaphthalene with CH₂NHR² group, (R¹)ₙ, Y-Ar, and (   )ₘ]

wherein:
X is a leaving group;
R² is: —C(O)—Rᶜ or —SO₂—Rᶜ wherein Rᶜ is $C_{1-6}$alkyl or —NRᵈRᵉ wherein Rᵈ and Rᵉ each independently is hydrogen or $C_{1-6}$alkyl; and
m, n, Y, Ar and R¹ are as recited in claim 10.

14. The method of claim 13, wherein the compound of formula n is urea.

15. The method of claim 13, wherein the compound of formula n is acetic anhydride.

16. The method of claim 13, further comprising:
oxidizing a dihydronaphthalene carbonitrile compound h h

[Structure: dihydronaphthalene with CN group, (R¹)ₙ, Y-Ar, and (   )ₘ]

to form the compound of formula i i

[Structure: dihydronaphthalene with C(O)NH₂ group, (R¹)ₙ, Y-Ar, and (   )ₘ]

wherein m, n, Y, Ar and R¹ are as recited in claim 13.

17. The method of claim 14, further comprising:
treating a compound of formula g g

[Structure: tetralone with (R¹)ₙ, Y-Ar, and (   )ₘ]

with cyanate, followed by treatment with sulfuric acid, to form the compound of formula i
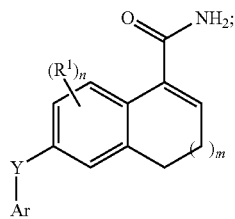
wherein m, n, Y, Ar and $R^1$ are as recited in claim 14.
* * * * *